US012624336B2

(12) United States Patent
Xu et al.

(10) Patent No.: US 12,624,336 B2

(45) Date of Patent: *May 12, 2026

(54) METHODS OF PRODUCING RECOMBINANT PROTEINS

(71) Applicant: Bristol-Myers Squibb Company, Princeton, NJ (US)

(72) Inventors: Jianlin Xu, Littleton, MA (US); Andrew Yongky, Medford, MA (US); Jun Tian, Westford, MA (US); Michael C. Borys, Groton, MA (US); Zhengjian Li, Sudbury, MA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 1247 days.

This patent is subject to a terminal disclaimer.

(21) Appl. No.: 17/252,163

(22) PCT Filed: Jul. 2, 2019

(86) PCT No.: PCT/US2019/040298

§ 371 (c)(1),
(2) Date: Dec. 14, 2020

(87) PCT Pub. No.: WO2020/010080

PCT Pub. Date: Jan. 9, 2020

(65) Prior Publication Data

US 2021/0253996 A1 Aug. 19, 2021

Related U.S. Application Data

(60) Provisional application No. 62/693,606, filed on Jul. 3, 2018.

(51) Int. Cl.
| | |
|---|---|
| *C12N 5/00* | (2006.01) |
| *C07K 16/00* | (2006.01) |
| *C12P 21/00* | (2006.01) |

(52) U.S. Cl.
CPC ............ *C12N 5/0018* (2013.01); *C07K 16/00* (2013.01); *C12P 21/00* (2013.01); *C07K 2317/14* (2013.01); *C12N 2500/34* (2013.01)

(58) Field of Classification Search
CPC .................. C12N 5/0018; C07K 16/00; C07K 2317/14; C12P 21/00
See application file for complete search history.

(56) References Cited

U.S. PATENT DOCUMENTS

| | | | |
|---|---|---|---|
| 4,515,893 A | 5/1985 | Kung et al. | |
| 5,091,313 A | 2/1992 | Chang | |
| 5,622,700 A | 4/1997 | Jardieu et al. | |
| 5,672,347 A | 9/1997 | Aggarwal et al. | |
| 5,693,762 A | 12/1997 | Queen et al. | |
| 5,714,338 A | 2/1998 | Wai Fei et al. | |
| 5,721,108 A | 2/1998 | Robinson et al. | |
| 5,725,856 A | 3/1998 | Hudziak et al. | |
| 5,736,137 A | 4/1998 | Anderson et al. | |
| 8,455,246 B2 | 6/2013 | Gorfien et al. | |
| 2014/0255993 A1* | 9/2014 | Follstad ................... C07K 1/14 | 435/69.6 |
| 2017/0107553 A1* | 4/2017 | Kottakota ............ C07K 16/241 | |
| 2017/0114381 A1* | 4/2017 | Goudar .................. C07K 16/00 | |

FOREIGN PATENT DOCUMENTS

| | | |
|---|---|---|
| EP | 0420937 B1 | 11/1994 |
| EP | 3818078 B1 | 2/2024 |
| GB | 2251249 A | 7/1992 |
| JP | 2015133980 A | 7/2015 |
| JP | 2016000030 A | 1/2016 |
| JP | 2018076286 A | 5/2018 |
| WO | WO-9304173 A1 | 3/1993 |
| WO | WO-9519181 A1 | 7/1995 |
| WO | WO-9523865 A1 | 9/1995 |

(Continued)

OTHER PUBLICATIONS

Xu, Sen, et al. "Bioreactor productivity and media cost comparison for different intensified cell culture processes." Biotechnology Progress 33.4 (2017): 867-878. (Year: 2017).*

Abaandou, Laura, David Quan, and Joseph Shiloach. "Affecting HEK293 cell growth and production performance by modifying the expression of specific genes." Cells 10.7 (2021): 1667. (Year: 2021).*

Padawer, Ishai, Wai Lam W. Ling, and Yunling Bai. "Case study: an accelerated 8-day monoclonal antibody production process based on high seeding densities." Biotechnology progress 29.3 (2013): 829-832. (Year: 2013).*

Pohlscheidt, Michael, et al. "Optimizing capacity utilization by large scale 3000 L perfusion in seed train bioreactors." Biotechnology progress 29.1 (2013): 222-229. (Year: 2013).*

Kshirsagar, Rashmi, and Thomas Ryll. "Innovation in cell banking, expansion, and production culture." New bioprocessing strategies: Development and manufacturing of recombinant antibodies and proteins (2018): 51-74. (Year: 2018).*

(Continued)

*Primary Examiner* — Teresa E Knight
*Assistant Examiner* — Michael Angelo Riga
(74) *Attorney, Agent, or Firm* — Sterne, Kessler, Goldstein, & Fox P.L.L.C.

(57) ABSTRACT

In certain embodiments, this disclosure provides novel methods of increasing the viable cell density of an N–1 large-scale bioreactor cell culture, comprising culturing a host cell expressing a recombinant poly peptide of interest in a non-perfusion-based culture system, and wherein the viable cell density is increased to at least $5 \times 10^6$ cells/mL. In certain embodiments, the disclosure provides novel methods for large-scale production of a recombinant polypeptide of interest, comprising: (1) culturing a host cell expressing a recombinant polypeptide of interest in an N–1 stage in a non-perfusion-based culture system, wherein the viable cell density is increased to at least $5 \times 10^6$ cells/mL; and (2) culturing N fed-batch production cells in an enriched media with high-seed density at least $1.5 \times 10^6$ cells/mL, wherein the N fed-batch production cells are inoculated from the N-1 stage in a non-perfusion-based culture system.

13 Claims, 17 Drawing Sheets

(56) References Cited

FOREIGN PATENT DOCUMENTS

| WO | WO-9630046 A1 | 10/1996 |
| WO | WO-9640210 A1 | 12/1996 |
| WO | WO-9726912 A2 | 7/1997 |
| WO | WO-9806248 A2 | 2/1998 |
| WO | WO-9823761 A1 | 6/1998 |
| WO | WO-9845331 A2 | 10/1998 |
| WO | WO-9851793 A1 | 11/1998 |
| WO | WO-9901556 A2 | 1/1999 |
| WO | WO-0075348 A1 | 12/2000 |
| WO | WO-0140309 A2 | 6/2001 |
| WO | WO-2006026408 A2 | 3/2006 |
| WO | WO-2006026445 A1 | 3/2006 |
| WO | WO-2008033517 A2 | 3/2008 |
| WO | WO-2008063892 A2 | 5/2008 |
| WO | WO-2009023562 A2 | 2/2009 |
| WO | WO-2011062926 A2 | 5/2011 |
| WO | WO-2012109162 A1 | 8/2012 |
| WO | WO-2012149197 A2 | 11/2012 |
| WO | WO-2015095809 A1 | 6/2015 |
| WO | WO-2015186075 A1 | 12/2015 |
| WO | WO-2017146646 A1 | 8/2017 |
| WO | WO-2017175086 A1 | 10/2017 |
| WO | WO-2018039499 A1 | 3/2018 |
| WO | WO-2020010080 A1 | 1/2020 |

OTHER PUBLICATIONS

Bird, R.E., et al., "Single-chain antigen-binding proteins," Science 242(4877):423-426, Association for the Advancement of Science, United States (Oct. 1988).

Carter, P., et al., "Humanization of an anti-p185HER2 antibody for human cancer therapy," Proceedings of the National Academy of Sciences USA 89(10):4285-4289, National Academy of Sciences, United States (May 1992).

Ceriani, R., et al., "Biological activity of two humanized antibodies against two different breast cancer antigens and comparison to their original murine forms," Cancer Research, 55(23 Suppl):5852s-5856s, American Association for Cancer Research, United States (Dec. 1995).

Choy, H., et al., "Percentage of anti-CD4 monoclonal antibody-coated lymphocytes in the rheumatoid joint is associated with clinical improvement. Implications for the development of immunotherapeutic dosing regimens," Arthritis and Rheumatism, 39(1):52-56, Wiley-Blackwell, United States (Jan. 1996).

Dhainaut, J., et al., "CDP571, a humanized antibody to human tumor necrosis factor-alpha: safety, pharmacokinetics, immune response, and influence of the antibody on cytokine concentrations in patients with septic shock. CPD571 Sepsis Study Group," Critical Care Medicine, 23(9):1461-9, Lippincott Williams & Wilkins, United States (Sep. 1995).

Ellis, J., et al., "Engineered anti-CD38 monoclonal antibodies for immunotherapy of multiple myeloma," Journal of Immunology, 155(2):925-937, American Association of Immunologists, United States (1995).

Graham, F.L., et al., "Characteristics of a human cell line transformed by DNA from human adenovirus type 5," The Journal of General Virology 36(1):59-74, Society For General Microbiology, United Kingdom (Jul. 1977).

Graziano, R., et al., "Construction and characterization of a humanized anti-gamma-Ig receptor type I (Fc gamma RI) monoclonal antibody," Journal of Immunology, 155(10):4996-5002, American Association of Immunologists, United States (1995).

Hourmant, M., et al., "Administration of an anti-CD11a monoclonal antibody in recipients of kidney transplantation. A pilot study," Transplantation, 58(3):377-80, Lippincott Williams & Wilkins, United States (1994).

Huston, J.S., et al., "Protein engineering of antibody binding sites: recovery of specific activity in an anti-digoxin single-chain Fv analogue produced in Escherichia coli," Proceedings of the National Academy of Sciences USA 85(16):5879-5883, National Academy of Sciences, United States (Aug. 1988).

International Search Report and Written Opinion for International Application No. PCT/US2019/040298, European Patent Office, Netherlands, mailed on Oct. 8, 2019, 10 pages.

Jurcic, J., et al., "Radiolabeled anti-CD33 monoclonal antibody M195 for myeloid leukemias," Cancer Research, 55(23 Suppl):5908s-5910s, American Association for Cancer Research, United States (1995).

Juweid, M., et al., "Treatment of non-Hodgkin's lymphoma with radiolabeled murine, chimeric, or humanized LL2, an anti-CD22 monoclonal antibody," Cancer Research, 55(23 Suppl):5899s-5907s, American Association for Cancer Research, United States (1995).

Kim, K., et al., "The vascular endothelial growth factor proteins: identification of biologically relevant regions by neutralizing monoclonal antibodies," Growth Factors, 7(1):53-64, Informa Healthcare, United Kingdom (1992).

Litton, M., et al., "Antibody-targeted superantigen therapy induces tumor-infiltrating lymphocytes, excessive cytokine production, and apoptosis in human colon carcinoma," European Journal of Immunology, 26(1):1-9, Wiley-VCH, Germany (1996).

Lorenz, H., et al., "In vivo blockade of TNF-alpha by intravenous infusion of a chimeric monoclonal TNF-alpha antibody in patients with rheumatoid arthritis. Short term cellular and molecular effects," Journal of Immunology 156(4):1646-1653, American Association of Immunologists, United States (1996).

Lu, F., et al., "Automated dynamic fed-batch process and media optimization for high productivity cell culture process development," Biotechnology and Bioengineering, 110(1):191-205, Wiley, United States (Jan. 2013).

Mather, J.P., "Establishment and Characterization of Two Distinct Mouse Testicular Epithelial Cell Lines," Biology of Reproduction 23(1):243-252, Society for the Study of Reproduction, United States (Aug. 1980).

Mather, J.P., et al., "Culture of Testicular Cells in Hormone-Supplemented Serum-Free Medium," Annals of the New York Academy of Sciences 383:44-68, Wiley-Blackwell, United States (1982).

Pohlscheidt, M., et al., "Optimizing Capacity Utilization by Large Scale 3000 L Perfusion in Seed Train Bioreactors," Biotechnology Progress 29(1):222-229, Wiley-Blackwell, United States (Jan. 2013).

Presta, L.G., et al., "Humanization of an Antibody Directed Against IgE," The Journal of Immunology 151(5):2623-2632, The American Association of Immunologists, Inc., United States (Sep. 1993).

Richman, C., et al., "Radioimmunotherapy for breast cancer using escalating fractionated doses of 131I-labeled chimeric L6 antibody with peripheral blood progenitor cell transfusions," Cancer research, 55(23 Suppl):5916s-5920s, American Association for Cancer Research, United States (Dec. 1995).

Riechmann, L., et al., "Reshaping human antibodies for therapy," Nature 332(6162):323-327, Nature Publishing Group, United Kingdom (Mar. 1988).

Sharkey, R., et al., "Evaluation of a complementarity-determining region-grafted (humanized) anti-carcinoembryonic antigen monoclonal antibody in preclinical and clinical studies," Cancer research, 55(23 Suppl):5935s-5945s, American Association for Cancer Research, United States (Dec. 1995).

St. John, R. C., et al., "Immunologic therapy for ARDS, septic shock, and multiple-organ failure," Chest, 103(3):932-943, Elsevier, United States (1993).

Stoppa, A.M, et al., "Anti-LFA1 monoclonal antibody (25.3) for treatment of steroid-resistant grade III-IV acute graft-versus-host disease," Transplant International, 4(1):3-7, Blackwell Publishing, United Kingdom (Apr. 1991).

Urlaub, G. and Chasin, L.A., "Isolation of Chinese Hamster Cell Mutants Deficient in Dihydrofolate Reductase Activity," Proceedings of the National Academy of Sciences USA 77(7):4216-4220, National Academy of Sciences, United States (Jul. 1980).

Ward, E.S., et al., "Binding Activities of a Repertoire of Single Immunoglobulin Variable Domains Secreted from Escherichia coli," Nature 341(6242):544-546, Nature Publishing Group, United Kingdom (Oct. 1989).

(56)                    References Cited

OTHER PUBLICATIONS

Xu, S., et al., "Bioreactor productivity and media cost comparison for different intensified cell culture processes," Biotechnology Progress, 33(4):867-878, Wiley-Blackwell, United States (Jan. 2017).
Yang, C., et al., "Perfusion seed cultures improve biopharmaceutical fed-batch production capacity and product quality," Biotechnology Progress, 30(3):616-625, Wiley-Blackwell, United States (May 2014).
Yongky, A., et al., "A novel high density N-1 batch seed strategy development for CHO cell culture manufacturing," 255th ACS National Meeting & Exposition, 255: BIOT487, American Chemical Society, United States (Mar. 2018).
Yongky, A., et al., "Process intensification in fed-batch production bioreactors using non-perfusion seed cultures," Monoclonal Antibodies, 11(8):1502-1514, Taylor & Francis, United States (Aug. 2019).
Insect Cell Biotechnology, pp. 291-298, Peng, J., et al., eds., Central China Normal University Press, China (Dec. 2010).
Fermentation Engineering and Equipment, pp. 161-166, Qiu, L., et al., eds., China Agriculture Press, China (Aug. 2007).
Modern Pharmaceutical Technology, pp. 252-254, Yuan Y., et al., eds., Chemical Industry Press, China (Jul. 2004).
Introduction to Modern Biotechnology, pp. 83-91, Zheng, A., et al., eds., Chongqing University Press, China (Aug. 2016).
English translation of Office Action for Chinese Patent Application No. 2019800449083, dated Jul. 2, 2025, The State Intellectual Property Office of China, China, 13 pages.
Abu-Absi, S., et al., "Cell Culture Process Operations for Recombinant Protein Production," Advances in Biochemical Engineering Biotechnology, 35-68, Springer Nature, Germany (Oct. 2013).
American Chemical Society, "Nexus of Food Energy and Water," 255th American Chemical Society National Meeting and Exposition, 1-4, United States (Mar. 2018).
"BalanCD® CHO Feed 2: Chemically-Defined Feed Medium," BioProcess Online, accessed at https://www.bioprocessonline.com/doc/balancd-cho-feed-2-0002, accessed on Oct. 17, 2024, 1 page.
Burteau, C.C., et al., "Fortification of a Protein-Free Cell Culture Medium with Plant Peptones Improves Cultivation and Productivity of an Interferon-Gamma-Producing CHO Cell Line," In Vitro Cellular & Developmental Biology. Animal 39(7):291-296, Springer, Germany (2003).
Butler, M., "Animal Cell Cultures: Recent Achievements and Perspectives in the Production of Biopharmaceuticals," Applied Microbiology and Biotechnology 68(3):283-291, Springer International, Germany (2005).
Cacciuttolo, M., "Perfusion or fed-batch? A matter of perspective," in Cell Culture and Upstream Processing, Butler, M., ed., pp. 173-184, Taylor and Francis, United Kingdom (2007).
Cayli, A., "Towards a Single-use protein production process," Slides of the oral presentation of at the ESACT meeting in Vienna May 15, 2011, 17 pages.
Chmiel, H., "Bioprocess Engineering," pp. 350, Spektrum, Berlin, Germany (2006), 4 pages.
Communication of Notice of Opposition against European Application No. 19745845.8, dated Dec. 4, 2024, European Patent Office, Germany, 48 pages.
Communication of Notice of Opposition against European Application No. 19745845.8, dated Dec. 4, 2024, European Patent Office, Germany, 66 pages.
Communication of Notice of Opposition against European Application No. 19745845.8, dated Dec. 2, 2024, European Patent Office, Germany, 51 pages.
Communication of Notice of Opposition against European Application No. 19745845.8, dated Dec. 3, 2024, European Patent Office, Germany, 24 pages.
Communication of Notice of Opposition against European Application No. 19745845.8, dated Nov. 29, 2024, European Patent Office, Germany, 33 pages.

Costa, A.R., et al., "Feed Optimization in Fed-batch Culture," Methods in Molecular Biology 1104:105-116, Humana Press, United States (2014).
Drapeau, D., et al., "Extracellular Insulin Degrading Activity Creates Instability in a CHO-based Batch-refeed Continuous Process," Cytotechnology 15(1-3):103-119, Kluwer Academic Publishers, United States (1994).
Gagnon, M., et al., "High-end pH-controlled Delivery of Glucose Effectively Suppresses Lactate Accumulation in CHO Fed-batch Cultures," Biotechnology and Bioengineering 108(6):1328-1337, Wiley, United States (Jun. 2011).
Hecht, V., et al., "Efficiency Improvement of an Antibody Production Process by Increasing the Inoculum Density," Biotechnology Progress 30(3):607-615, Wiley-Blackwell, United States (May-Jun. 2014).
Hiller G.W., et al., "Cell-Controlled Hybrid Perfusion Fed-Batch CHO Cell Process Provides Significant Productivity Improvement Over Conventional Fed-Batch Cultures," Biotechnology and Bioengineering, 114(7):1438-1447, Wiley, United States (Jul. 2017).
Hu, W., "Cell Culture Bioprocess Engineering", CRC Press, Boca Raton, United States (2012), 337 pages.
Huang, Y.M., et al., "Maximizing Productivity of CHO Cell-based Fed-batch Culture Using Chemically Defined Media Conditions and Typical Manufacturing Equipment," Biotechnology Progress 26(5):1400-1410, Wiley-Blackwell, United States (Sep. 2010).
Irvine Scientific, "BalanCD™ CHO Feed 2," Information Leaflet, 1-7, (2012), 7 pages.
Kantardjieff, A., et al., "Mammalian Cell Cultures for Biologics Manufacturing," Advances in Biochemical Engineering/biotechnology 139:1-9, Springer Verlag, Germany (2014).
Kern, S., et al., "Model-based Strategy for Cell Culture Seed Train Layout Verified at Lab Scale," Cytotechnology 68(4):1019-1032, Kluwer Academic Publishers, United States (Aug. 2016).
Kim Y.J., et al., "Rich Production Media as a Platform for CHO Cell Line Development," AMB Express 10(1):93, Springer-Verlag, Germany (May 2020), 13 pages.
Kloth, C., et al., "Inoculum Expansion Methods, Recombinant Mammalian Cell Lines" in The Encyclopedia of Industrial Biotechnology: Bioprocess, Bioseparation, and Cell Technology, vol. 5, Flicking, M.C., ed., pp. 2988-3000, Wiley, Hoboken, United States (2010).
Kompala, D.S., and Ozturk, S.S., "Optimization of High Cell Density Perfusion Bioreactors," in Cell Culture Technology for Pharmaceutical and Cell-Based Therapies, Oztruk, S.S., et al., ed., pp. 387-416, Taylor and Francis, Abingdon, United Kingdom (2005).
Kshirsagar, R., and Ryll, T., "Innovation in Cell Banking, Expansion, and Production Culture," Advances in Biochemical Engineering/biotechnology 165:51-74, Springer Verlag, Germany (2018).
Kumar, N., et al., "Proliferation Control Strategies to Improve Productivity and Survival During CHO Based Production Culture: a Summary of Recent Methods Employed and the Effects of Proliferation Control in Product Secreting CHO Cell Lines," Cytotechnology 53(1-3):33-46, Kluwer Academic Publishers, United States (Apr. 2007).
Landauer, K., "Designing Media for Animal Cell Culture: CHO Cells, the Industrial Standard," in Animal Cell Biotechnology: Methods and Protocols,Portner, R., ed., pp. 89-103, Springer, Berlin, Germany (2014).
Landauer, K., et al., "Development of a Chemically Defined CHO Medium by Engineering Based on a Feed Solution," BMC Proceedings 5(Suppl 8):2 pages, BioMed Central, United Kingdom (2011).
Li, F., et al., "Cell Culture Processes for Monoclonal Antibody Production, " mAbs 2(5):466-479, Taylor & Francis, Landes Bioscience, United States (Sep.-Oct. 2010).
Li, F., et al., "Current Therapeutic Antibody Production and Process Optimization," BioProcessing Journal 4(5):23-30; BioProcessing Journal, United States (2005).
Lin, H-H., et al., "High Glucose Enhances CAPM Level and Extracellular Signal-regulated Kinase Phosphorylation in Chinese Hamster Ovary Cell: Usage of Br-cAMP in Foreign Protein

(56) References Cited

OTHER PUBLICATIONS

β-galactosidase Expression," Journal of Bioscience and Bioengineering 124(1):108-114, Society for Biotechnology, Japan (Jul. 2017).

Muller, D., et al., "Continuous Perfusion versus Discontinuous Fed-Batch," in *Animal Cell Technology: From Target to Market*, Lindner-Olsson, E., et al., ed., pp. 293-299, Kluwer Academic Publishers, United States (2001).

Mulukutla B.C., et al., "On Metabolic Shift to Lactate Consumption in Fed-Batch Culture of Mammalian Cells," Metabolic Engineering 14(2):138-149, Academic Press, United States (Mar. 2012).

Ozturk, S.S., and Hu, W.S., "Cell Culture Technology for Pharmaceutical and Cell-based Therapies," Taylor and Francis, Abingdon, United Kingdom (2005), 784 pages.

Ozturk, S.S., "Equipment for Large-scale Mammalian Cell Culture," Advances in Biochemical Engineering/biotechnology 139:69-92, Springer Verlag, Germany (2014).

Padawer, I., et al., "Case Study: An Accelerated 8-day Monoclonal Antibody Production Process Based on High Seeding Densities," Biotechnology Progress 29(3):829-832, Wiley-Blackwell, United States (May 2013).

Pan, X., et al., "Selection of Chemically Defined Media for CHO Cell Fed-batch Culture Processes," Cytotechnology 69(1):39-56, Kluwer Academic Publishers, United States (Feb. 2017).

Pastorian, K.E., and Byus, C.V., "Tolerance to Putrescine Toxicity in Chinese Hamster Ovary Cells is Associated With Altered Uptake and Export," Experimental Cell Research 231(2):284-295, Academic Press, United States (Mar. 1997).

Reinhart, D., et al., "Benchmarking of Commercially Available CHO Cell Culture Media for Antibody Production," Applied Microbiology and Biotechnology 99(11):4645-4657, Springer International, Germany (Jun. 2015).

Ritacco, F.V., et al., "Cell Culture Media for Recombinant Protein Expression in Chinese Hamster Ovary (CHO) Cells: History, Key Components, and Optimization Strategies," Biotechnology Progress 34(6):1407-1426, Wiley-Blackwell, United States (Nov. 2018).

Sakai, K., et al., "Effects of Phospholipids on Growth of Chinese Hamster Ovary Cells in Serum-free Media," Journal of Bioscience and Bioengineering 88(3):306-309, Society for Biotechnology, Japan (1999).

Sauer, P.W., et al., "A High-yielding, Generic Fed-batch Cell Culture Process for Production of Recombinant Antibodies," Biotechnology and Bioengineering 67(5):585-597, Wiley, United States (Mar. 2000).

Seth, G., et al., "Development of a New Bioprocess Scheme using Frozen Seed Train Intermediates to Initiate CHO Cell Culture Manufacturing Campaigns," Biotechnology Progress 110(5):1376-1385, Wiley, United States (May 2013).

Tang, Y., et al., "Fed-batch Performance Profiles for Mab Production Using Different Intensified N-1 Seed Strategies Are Cho Cell-line Dependent," Biotechnology Progress 40(4):e3446, 1-10, American Institute of Chemical Engineers, United States (Jul.-Aug. 2024).

Torkashvand, F., et al., "Designed Amino Acid Feed in Improvement of Production and Quality Targets of a Therapeutic Monoclonal Antibody," PloS one 10(10):e0140597, Public Library of Science, United States (Oct. 2015), 21 pages.

Whitaker, S.C., et al., "Validation of Continuously Perfused Cell Culture Processes for Production of Monoclonal Antibodies," in *Validation of Biopharmaceutical Manufacturing Processes*, Kelley, B.D., et al., ed., pp. 28-43, American Chemical Society, Washington, United States (1998).

Whitford, W. and Manwaring, J., "Lipids in Cell Culture Media," Fish. Appl. Notes, 152-154, (2004).

Whitford, W., et al., "NSO Serum-Free Culture and Applications," Bioprocess Technical, 1(12):36-47, (Dec. 2003).

Wright, B., et al., "A Novel Seed-Train Process Using High-Density Cell Banking, a Disposable Bioreactor, and Perfusion Technologies," BioProcess International 13(3):16-25, Informa, United States (Mar. 2015).

Xie, L., and Zhou, W., "Fedbatch Cultivation of Mammalian Cells for the Production of Recombinant Proteins," in *Cell Culture Technology for Pharmaceutical and Cell-Based Therapies*, Oztruk, S.S., et al., ed., pp. 349-386, Taylor and Francis, Abingdon, United Kingdom (2005).

Xing, Z., et al., "Optimizing Amino Acid Composition of Cho Cell Culture Media for a Fusion Protein Production," Process Biochemistry 46(7):1423-1429, Elsevier, Netherland (Mar. 2011).

Yee, J.C., et al., "Advances in Process Control Strategies for Mammalian Fed-batch Cultures," Current Opinion in Chemical Engineering 22:34-41, Elsevier, Netherland (2018).

Yee, J.C., et al., "Process Improvment of a High Density Fed-batch Process Using N-1 Perfusion Seed Cultures," BIOT Abstract 487, 2 Pages, (Mar. 2018).

Zhou, W., et al., "High Viable Cell Concentration Fed-Batch Cultures of Hybridoma Cells through on-Line Nutrient Feeding," Biotechnology and Bioengineering 46(6):579-587, Wiley, United States (Jun. 1995).

Zhu, M.M., et al., "Effects of Elevated Pco2 and Osmolality on Growth of Cho Cells and Production of Antibody-fusion Protein B1: a Case Study," Biotechnology Progress 21(1):70-77, Wiley-Blackwell, United States (Jan.-Feb. 2005).

Co-pending U.S. Appl. No. 19/030,272, inventors Xu, J., et al., filed Jan. 17, 2025 (Not yet Published).

Reinhart, D., et al., "Benchmarking of commercially available CHO cell culture media for antibody production", BMC Proceedings 7(Suppl 6):P13 (2013), 3 pages.

Product information of "Ex-CelITM 302", SAFC Biosciences (2006), 4 pages.

BioConcept Cell Culture Catalogue (2004), 82 pages.

* cited by examiner

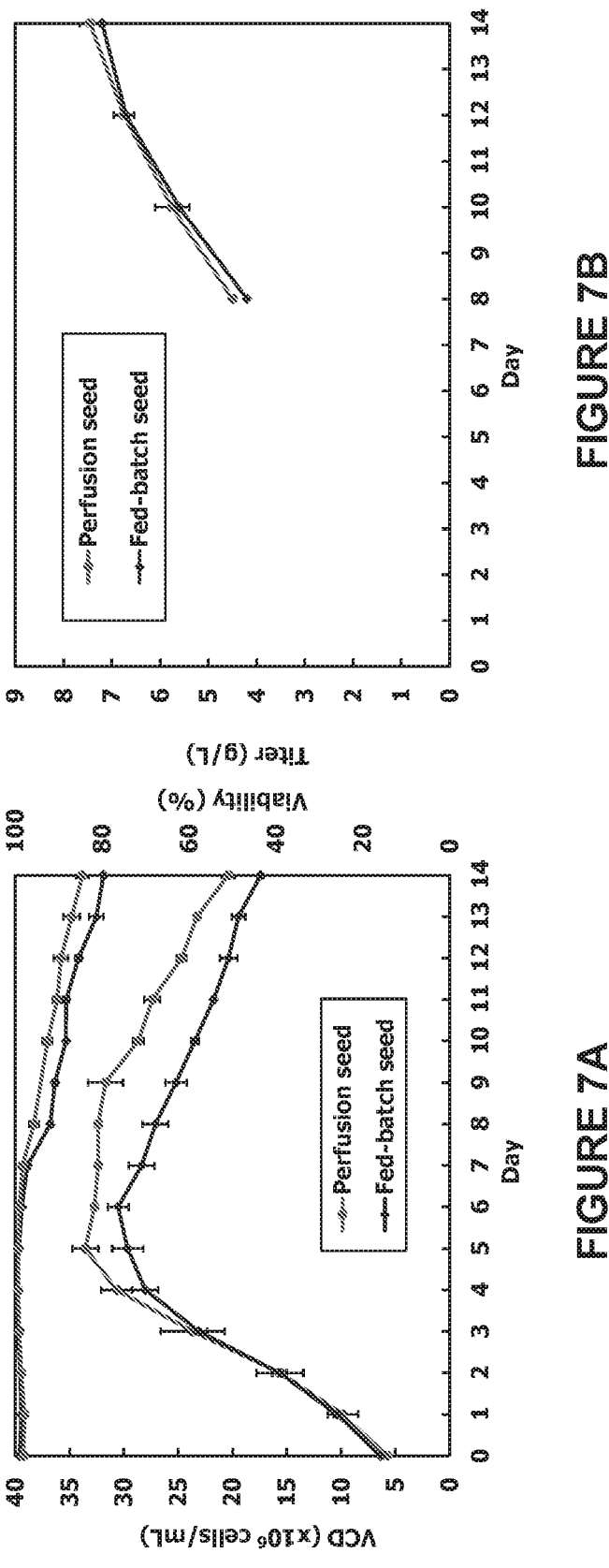

METHODS OF PRODUCING RECOMBINANT PROTEINS

CROSS REFERENCE TO RELATED APPLICATIONS

The present application is a U.S. National Stage of International Patent Application No. PCT/US2019/040298, filed Jul. 2, 2019, which claims the priority benefit of U.S. Provisional Application No. 62/693,606, filed Jul. 3, 2018, each of which is hereby incorporated by reference in their entirety.

FIELD OF INVENTION

The present invention generally relates to methods of increasing viable cell density during the N–1 culture stage with non-perfusion strategy for inoculation of N production bioreactors at high-seed density for cell culture manufacturing.

BACKGROUND

Proteins and polypeptides have become increasingly important as therapeutic agents. In most cases, therapeutic proteins and polypeptides are produced in cell culture, from cells that have been engineered and/or selected to produce unusually high levels of the polypeptide of interest. Control and optimization of cell culture conditions is critically important for successful commercial production of proteins and polypeptides.

Many proteins and polypeptides produced in cell culture are made in a fed-batch process, in which cells are cultured for a period of time, and then the culture is terminated and the produced protein or polypeptide is isolated. The ultimate amount and quality of protein or polypeptide produced can be dramatically affected by the N–1 seed culture and the seed-density at N production. While efforts have been made to improve production of proteins and polypeptides in fed-batch culture processes, there remains a need for additional improvements.

Perfusion cell culture can achieve much higher viable cell densities than conventional fed-batch cell culture systems. Perfusion cell culture provides a continuous supply of fresh media in the culture system, while removing waste products, which provides a rich environment for the cells to grow. In comparison to the conventional fed-batch production culture with low-seed density, the high-seed density fed-batch production culture inoculated with N–1 perfusion seed can achieve higher final titer within a short duration. However, perfusion cell culture becomes expensive when used in large-scale culture systems (e.g., greater than 200 L bioreactor) because of large quantities of cell culture media consumed. Also, perfusion cell culture can have complications from the cell retention system which prevents the cells from being removed from the cell culture system, especially for a large scale manufacturing.

There is a particular need for the development of improved systems for producing proteins and polypeptides by large-scale cell culture at high-seed cell density with non-perfusion systems.

BRIEF SUMMARY OF THE DISCLOSURE

The present disclosure is directed to a method of increasing the viable cell density of a N–1 large-scale bioreactor cell culture, comprising culturing a host cell expressing a recombinant polypeptide of interest in a non-perfusion-based culture system, and wherein the viable cell density is increased to at least $5\times10^6$ cells/mL. In some embodiments, the non-perfusion-based culture system is a batch or fed-batch bioreactor. In some embodiments, the viable cell density at an N–1 stage is at least $5\times10^6$, at least $10\times10^6$, at least $15\times10^6$, at least $20\times10^6$, at least $25\times10^6$, or at least $30\times10^6$ viable cells per mL. In some embodiments, the cell viability is at least 80% on the last day of the N–1 stage, at least 85% on the last day of the N–1 stage, or at least 90% on the last day of the N–1 stage.

In some embodiments of the invention, the host cell is cultured in an enriched media for an N–1 batch culture. In some embodiments, the host cell is cultured in a seed media with addition of a feed media for an N–1 fed-batch culture.

In some embodiments of the invention, the media is enriched by a feed media at least 5% relative to non-enriched media, at least 10% relative to non-enriched media, at least 15% relative to non-enriched media, or at least 20% relative to non-enriched media. In some embodiments, the enriched media or feed media comprises an increased amount of a carbon source. In some embodiments, the carbon source is glucose. In some embodiments, the enriched media or feed media comprises an increased amount of nutrients. In some embodiments, the nutrients are selected from amino acids, lipids, vitamins, minerals, and polyamines. In some embodiments, the enriched media comprises an increased amount of a carbon source and nutrients. In some embodiments, the carbon source is glucose and the nutrients are selected from amino acids, lipids, vitamins, minerals, and polyamines.

In some embodiments of the invention, the host cell is a mammalian cell. In some embodiments, the mammalian cell is selected from the group consisting of CHO, VERO, BHK, HEK, HeLa, COS, MDCK and hybridoma cells. In some embodiments, the host cell is a CHO cell.

In some embodiments of the invention, the polypeptide of interest is a therapeutic polypeptide. In some embodiments, the polypeptide of interest is an antibody or antigen-binding fragment. In some embodiments, the antibody or antigen-binding fragment binds an antigen selected from the group consisting of PD-1, PD-L1, LAG-3, TIGIT, GITR, CXCR4, CD73 HER2, VEGF, CD20, CD40, CD11a, tissue factor (TF), PSCA, IL-8, EGFR, HER3, and HER4.

In some embodiments of the invention, the bioreactor is at least 50 L, at least 500 L, at least 1,000 L, at least 5,000 L, or at least 10,000 L.

In some embodiments of the invention, the method further comprises culturing at least $5\times10^6$ viable cells per mL in the N–1 stage in enriched batch culture or fed-batch culture, which is used for inoculation of the N production stage to produce the recombinant polypeptide of interest. In some embodiments, the method further comprises the step of isolating the polypeptide of interest from the production culture system.

The present disclosure is also directed to a method for large-scale production of a recombinant polypeptide of interest comprising: (1) culturing a host cell expressing a recombinant polypeptide of interest in an N–1 stage in a non-perfusion-based culture system, wherein the viable cell density is increased to at least $5\times10^6$ cells/mL; and (2) culturing N fed-batch production cells in a basal media or an enriched basal media with high-seed density at least $1.5\times10^6$ cells/mL, wherein the N fed-batch production cells are inoculated from the N–1 stage in the non-perfusion-based culture system. In some embodiments, the N production culture system is a fed-batch bioreactor.

In some embodiments of the invention, the enriched basal media is enriched by a feed media at least 5%, at least 10%, at least 15%, at least 20% relative to non-enriched media. In some embodiments, the enriched media comprises an increased amount of a carbon source. In some embodiments, the carbon source is glucose. In some embodiments, the enriched media comprises an increased amount of nutrients. In some embodiments, the nutrients are selected from amino acids, lipids, vitamins, minerals, and polyamines. In some embodiments, the enriched media comprises an increased amount of a carbon source and nutrients. In some embodiments, the carbon source is glucose and the nutrients are selected from amino acids, lipids, vitamins, minerals, and polyamines.

In some embodiments of the invention, the bioreactor is at least 50 L, at least 500 L, at least 1,000 L, at least 5,000 L, at least 10,000 L, at least 15,000 L, or at least 20,000 L.

In some embodiments of the invention, the host cell is a mammalian cell. In some embodiments, the host cell is a CHO cell.

In some embodiments of the invention, the titer of the polypeptide of interest is at least 100 mg/L, at least 1 g/L, at least 3 g/L, at least 5 g/L or at least 10 g/L.

In some embodiments of the invention, the host cell is cultured in a basal media or an enriched basal media for N fed-batch production bioreactor to obtain a viable cell density of at least $1.5 \times 10^6$, at least $5 \times 10^6$, or at least $10 \times 10^6$ viable cells per mL.

In some embodiments of the invention, the method further comprises the step of isolating the polypeptide of interest. In some embodiments, the polypeptide of interest is a therapeutic polypeptide. In some embodiments, the polypeptide of interest is an antibody or antigen-binding fragment.

BRIEF DESCRIPTION OF THE DRAWINGS

FIG. 1A shows the viable cell density ("VCD") of an N–1 cell culture grown in the following cell culture systems for CHO cell line A: perfusion, fed-batch, batch, batch with enriched glucose, and batch with enriched glucose and nutrients cell culture systems. FIG. 1B shows cell viability (%) of N–1 cell cultures grown in the following cell culture systems for cell line A: perfusion, fed-batch, batch, batch with enriched glucose, and batch with enriched glucose and nutrients.

FIG. 2A shows the viable cell density of an N production culture for polypeptide-1 by cell line A using a seed culture from the following N–1 cell culture systems: perfusion, fed-batch, batch with enriched glucose, and batch with enriched glucose and nutrients. FIG. 2B shows the titer of the polypeptide of interest grown in a production culture using a seed culture from the following N–1 cell culture systems: perfusion, fed-batch, batch with enriched glucose, and batch with enriched glucose and nutrients. FIG. 2C shows imaged capillary isoelectric focusing ("iCIEF"), size-exclusion chromatography ("SEC"), and N-glycan analysis for the polypeptide of interest grown in a production culture for polypeptide-1 by CHO cell line A using a seed culture from the following N–1 cell culture systems: perfusion, fed-batch, batch with enriched glucose, and batch with enriched glucose and nutrients.

FIG. 3A shows the VCD of an N–1 cell culture grown in the following cell culture systems for CHO cell line B: perfusion, fed-batch, batch, batch with enriched glucose, and batch with enriched glucose and nutrients cell culture systems. FIG. 3B shows cell viability (%) of N–1 cell cultures grown in the following cell culture systems for CHO cell line B: perfusion, fed-batch, batch, batch with enriched glucose, and batch with enriched glucose and nutrients.

FIG. 4A shows the viable cell density of an N production culture for polypeptide-2 by CHO cell line B using a seed culture from the following N–1 cell culture systems: perfusion, fed-batch, batch with enriched glucose, and batch with enriched glucose and nutrients. FIG. 4B shows the titer of the polypeptide of interest grown in an N production culture for polypeptide-2 by CHO cell line B using a seed culture from the following N–1 cell culture systems: perfusion, fed-batch, batch with enriched glucose, and batch with enriched glucose and nutrients. FIG. 4C shows iCIEF, SEC, and N-glycan analysis for the polypeptide of interest grown in the N production culture for polypeptide-2 by CHO cell line B using a seed culture from the following N–1 cell culture systems: perfusion, fed-batch, batch with enriched glucose, and batch with enriched glucose and nutrients.

FIG. 5A shows the VCD of an N–1 cell culture grown in the following cell culture systems for CHO cell line C: perfusion, fed-batch, batch, batch with enriched glucose, and batch with enriched glucose and nutrients cell culture systems. FIG. 5B shows cell viability (%) of N–1 cell cultures grown in the following cell culture systems: perfusion, fed-batch, batch, batch with enriched glucose, and batch with enriched glucose and nutrients.

FIG. 6A shows the viable cell density of an N production culture for polypeptide-3 by CHO cell line C using a seed culture from the following N–1 cell culture systems: fed-batch and batch with enriched glucose and nutrients. FIG. 6B shows the titer of the polypeptide of interest grown in the production culture for polypeptide-3 by CHO cell line C using a seed culture from the following N–1 cell culture systems: fed-batch and batch with enriched glucose and nutrients. FIG. 6C shows iCIEF, SEC, and N-glycan analysis for the polypeptide of interest grown in the N production culture for polypeptide-3 by CHO cell line C using a seed culture from the following N–1 cell culture systems: fed-batch and batch with enriched glucose and nutrients.

FIGS. 7A-7C. FIG. 7A shows the viable cell density of an N production culture for polypeptide-3 by CHO cell line C using a seed culture from the following N–1 cell culture systems: perfusion and fed-batch. FIG. 7B shows the titer of the polypeptide of interest grown in the production culture for polypeptide-3 by CHO cell line C using the seed culture from the following N–1 cell culture systems: perfusion and fed-batch. FIG. 7C shows iCIEF, SEC, and N-glycan analysis for the polypeptide of interest grown in the N production culture for polypeptide-3 by CHO cell line C using a seed culture from the following N–1 cell culture systems: perfusion and fed-batch.

FIG. 8A shows the viable cell density of N production cultures at 1000 L scale (n=3) and 5 L satellites (n=2) for polypeptide-1 by CHO cell line A using a seed culture from the following N–1 cell culture system: batch with enriched glucose and nutrients. FIG. 8B shows the titer of the polypeptide of interest grown in the production cultures at 1000 L scale (n=3) and 5 L satellites (n=2) for polypeptide-1 by CHO cell line A using the seed culture from the following N–1 cell culture system: batch with enriched glucose and nutrients. FIG. 8C shows iCIEF, SEC, and N-glycan analysis for the polypeptide of interest grown in the N production cultures at 1000 L scale (n=3) and 5 L satellites (n=2) for polypeptide-1 by CHO cell line A using a seed culture from the following N–1 cell culture systems: batch with enriched glucose and nutrients.

FIG. 9A shows the viable cell density of N production cultures at 500 L scale (n=1) and 5 L satellites (n=2) for polypeptide-2 by CHO cell line B using a seed culture from the following N–1 cell culture system: batch with enriched glucose and nutrients. FIG. 9B shows the titer of the polypeptide of interest grown in the production cultures at 500 L scale (n=1) and 5 L satellites (n=2) for polypeptide-2 by CHO cell line B using the seed culture from the following N–1 cell culture system: batch with enriched glucose and nutrients. FIG. 9C shows iCIEF, SEC, and N-glycan analysis for the polypeptide of interest grown in the N production cultures at 500 L scale (n=1) and 5 L satellites (n=2) for polypeptide-2 by CHO cell line B using a seed culture from the following N–1 cell culture systems: batch with enriched glucose and nutrients.

FIG. 10A shows the viable cell density of N production cultures at 500 L scale (n=1) and 5 L satellites (n=2) for polypeptide-3 by CHO cell line C using a seed culture from the following N–1 cell culture system: fed-batch. FIG. 10B shows the titer of the polypeptide of interest grown in the production cultures at 500 L scale (n=1) and 5 L satellites (n=2) for polypeptide-3 by CHO cell line C using the seed culture from the following N–1 cell culture system: fed-batch. FIG. 10C shows iCIEF, SEC, and N-glycan analysis for the polypeptide of interest grown in the N production cultures at 500 L scale (n=1) and 5 L satellites (n=2) for polypeptide-3 by CHO cell line C using a seed culture from the following N–1 cell culture systems: fed-batch.

DETAILED DESCRIPTION OF THE INVENTION

Figures 1A, 1B:
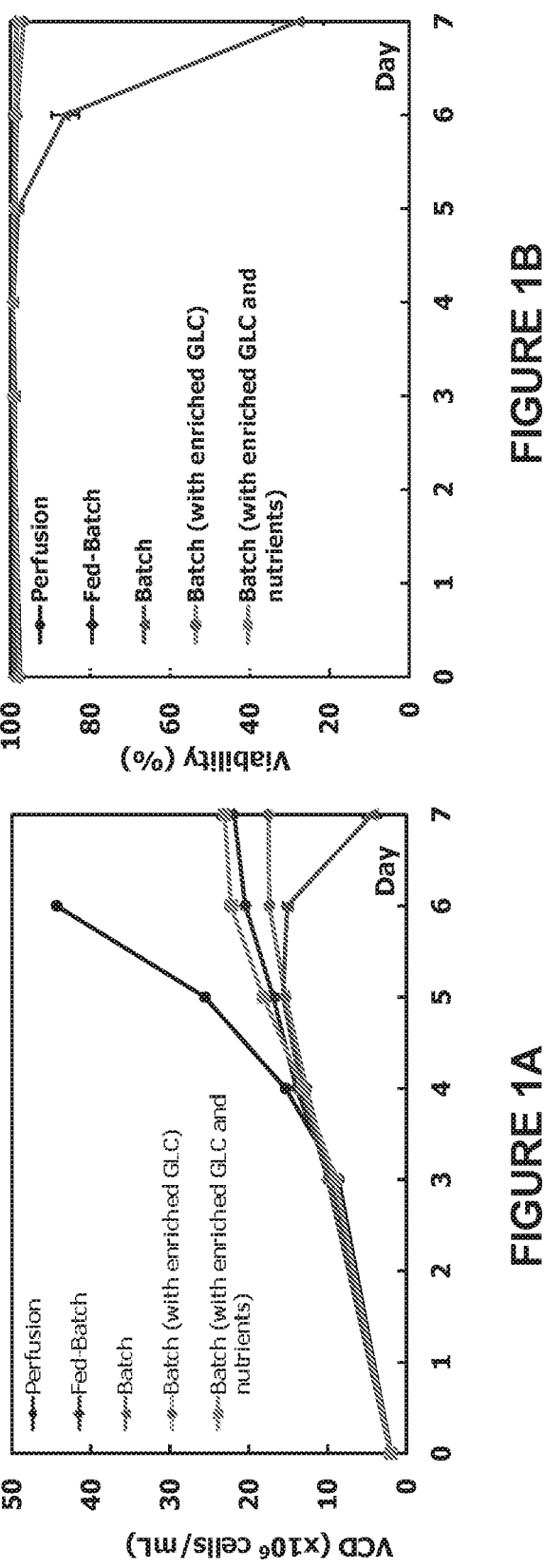
FIGS. 1A and 1B.

In certain embodiments, this disclosure provides novel methods of increasing the viable cell density of an N–1 large-scale bioreactor cell culture, comprising culturing a host cell expressing a recombinant polypeptide of interest in a non-perfusion-based culture system, and wherein the viable cell density is increased to at least $5\times10^6$ cells/mL. In certain embodiments, the disclosure provides novel methods for large-scale production of a recombinant polypeptide of interest, comprising: (1) culturing a host cell expressing a recombinant polypeptide of interest in an N–1 stage in a non-perfusion-based culture system, wherein the viable cell density is increased to at least $5\times10^6$ cells/mL; and (2) culturing the cells in an N production stage, which are inoculated from the N–1 cell culture in a non-perfusion culture system, in enriched media with high-seed density to at least $1.5\times10^6$ cells/mL.

Definitions

The indefinite articles "a" or "an" should be understood to refer to "one or more" of any recited or enumerated component.

The term "about" as used herein to a value or composition that is within an acceptable error range for the particular value or composition as determined by one of ordinary skill in the art, which will depend in part on how the value or composition is measured or determined, i.e., the limitations of the measurement system. For example, "about" can mean within 1 or more than 1 standard deviation per the practice in the art. Alternatively, "about" can mean a range of up to 20%. Furthermore, particularly with respect to biological systems or processes, the terms can mean up to an order of magnitude or up to 5-fold of a value. When particular values or compositions are provided in the application and claims, unless otherwise stated, the meaning of "about" should be assumed to be within an acceptable error range for that particular value or composition.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone). The use of the alternative (e.g., "or") should be understood to mean either one, both, or any combination thereof of the alternatives.

As used herein, term "amino acid," in its broadest sense, refers to any compound and/or substance that can be incorporated into a polypeptide chain. In some embodiments, an amino acid has the general structure $H_2N$—$C(H)(R)$—$COOH$. In some embodiments, an amino acid is a naturally occurring amino acid. In some embodiments, an amino acid is a synthetic amino acid; in some embodiments, an amino acid is a D-amino acid; in some embodiments, an amino acid is an L-amino acid. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc. In some embodiments, amino acids of the present invention may be provided in or used to supplement medium for cell cultures. In some embodiments, amino acids provided in or used to supplement cell culture medium may be provided as salts or in hydrate form.

The term "antibody" as used herein refers to an immunoglobulin molecule that recognizes and specifically binds a target, such as a protein, polypeptide, peptide, carbohydrate, polynucleotide, lipid, or combinations of the foregoing, through at least one antigen recognition site within the variable region of the immunoglobulin molecule. As used herein, the term encompasses intact polyclonal antibodies, intact monoclonal antibodies, antibody fragments (such as Fab, Fab', F(ab')2, and Fv fragments), single chain Fv (scFv) antibodies, multispecific antibodies such as bispecific antibodies generated from at least two intact antibodies, monospecific antibodies, monovalent antibodies, chimeric antibodies, humanized antibodies, human antibodies, fusion proteins comprising an antigen determination portion of an antibody, and any other modified immunoglobulin molecule comprising an antigen recognition site as long as the antibodies exhibit the desired biological activity. An antibody can be any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well-known subunit structures and three-dimensional configurations. Antibodies can be naked or conjugated to other molecules, including but not limited to, toxins and radioisotopes.

The term "antigen-binding portion" of an antibody, or an "antigen-binding fragment", as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding fragment", e.g., (i) a Fab fragment (fragment from papain cleavage) or a similar monovalent fragment consisting of the VL, VH, LC and CH1 domains; (ii) a F(ab')$_2$ fragment (fragment from pepsin cleavage) or a similar bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; (vi) an isolated complementarity determining region (CDR) and (vii) a combination of two or more isolated CDRs which can optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see, e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

The term "batch culture" as used herein refers to a method of culturing cells in which all the components that will ultimately be used in culturing the cells, including the medium (see definition of "medium" below) as well as the cells themselves, are provided at the beginning of the culturing process. A batch culture is typically stopped at some point and the cells and/or components in the medium are harvested and optionally purified. The term "fed-batch culture" means the incremental or continuous addition of a second liquid culture medium to an initial cell culture without substantial or significant removal of the first liquid culture medium from the cell culture. In some instances, the second liquid culture medium is the same as the first liquid culture medium. In other instances, the second liquid culture medium is a concentrated form of the first liquid culture medium and/or is added as a dry powder.

The term "bioreactor" as used herein refers to any vessel used for the growth of a mammalian cell culture. The bioreactor can be of any size so long as it is useful for the culturing of mammalian cells. Typically, the bioreactor will be at least 1 liter and may be 10, 100, 250, 500, 1000, 2500, 5000, 8000, 10,000, 12,000, 15,000, 20,000 liters or more, or any volume in between. The internal conditions of the bioreactor, including, but not limited to pH and temperature, are typically controlled during the culturing period. The bioreactor can be composed of any material that is suitable for holding mammalian cell cultures suspended in media under the culture conditions of the present invention, including glass, plastic or metal. The term "production bioreactor"

as used herein refers to the final bioreactor used in the production of the polypeptide or protein of interest. The volume of the large-scale cell culture production bioreactor is typically at least 500 liters and may be 1000, 2500, 5000, 8000, 10,000, 12,000, 15,000, 20,000 liters or more, or any volume in between. One of ordinary skill in the art will be aware of and will be able to choose suitable bioreactors for use in practicing the present invention.

The term "viable cell density" as used herein refers to that number of viable (living) cells present in a given volume of medium. The term "target cell density" means a specific concentration of cells per volume of culture medium for producing a recombinant protein in culture. Target cell density can vary depending upon the specific mammalian cell cultured.

The term "cell viability" as used herein refers to the ability of cells in culture to survive under a given set of culture conditions or experimental variations. The term as used herein also refers to that portion of cells which are alive at a particular time in relation to the total number of cells, living and dead, in the culture at that time.

The terms "culture", "cell culture" and "mammalian cell culture" as used herein refer to a mammalian cell population that is suspended in a medium under conditions suitable to survival and/or growth of the cell population. As will be clear to those of ordinary skill in the art, these terms as used herein may refer to the combination comprising the mammalian cell population and the medium in which the population is suspended.

The term "culturing" or "cell culturing" means the maintenance or growth of a mammalian cell in a liquid culture medium under a controlled set of physical conditions.

The terms "medium", "cell culture medium", "culture medium" as used herein refer to a solution containing nutrients which nourish growing mammalian cells. Typically, these solutions provide essential and non-essential amino acids, vitamins, energy sources, lipids, and trace elements required by the cell for minimal growth and/or survival. The solution may also contain components that enhance growth and/or survival above the minimal rate, including hormones and growth factors. The solution is preferably formulated to a pH and salt concentration optimal for cell survival and proliferation. The medium may also be a "chemically-defined media"—a serum-free media that contains no proteins, hydrolysates or components of unknown composition. Defined media are free of animal-derived components and all components have a known chemical structure. The term "enriched medium", "enriched media", or "enriched chemically-defined medium" is culture media that comprises additional or increased amounts of carbon sources and/or nutrients relative to the standard culture media.

The term "N−1 stage" as used herein refers to the last seed expansion stage right before production inoculation. The N−1 stage is the final cell growth step before seeding the production bioreactor for polypeptide production. The terms "N−2 stage" and "N−3 stage" as used herein refers to the period of time during cell growth and expansion and, typically, before inoculation of N production stage. The N−3 stage is the cell growth stage used to increase viable cell density to be used in the N−2 stage. The N−2 stage is the cell growth stage used to increase viable cell density to be used in the N−1 stage.

The term "perfusion" or "perfusion process" as used herein refers to a method of culturing cells in which equivalent volumes of media (containing nutritional supplements) are simultaneously added and removed from the bioreactor while the cells are retained in the reactor. A volume of cells and media corresponding to the supplement media is typically removed on a continuous or semi-continuous basis and is optionally purified. Typically, a cell culture process involving a perfusion process is referred to as "perfusion culture." In some embodiments, a fresh medium may be identical or similar to the base medium used in the cell culture process. In some embodiments, a fresh medium may be different than the base medium but contain the desired nutritional supplements. In some embodiments, a fresh medium is a chemically-defined medium.

The terms "polynucleotide" or "nucleotide" as used herein are intended to encompass a singular nucleic acid as well as plural nucleic acids, and refers to an isolated nucleic acid molecule or construct, e.g., messenger RNA (mRNA), complementary DNA (cDNA), or plasmid DNA (pDNA). In certain aspects, a polynucleotide comprises a conventional phosphodiester bond or a non-conventional bond (e.g., an amide bond, such as found in peptide nucleic acids (PNA)).

The term "polypeptide" as used herein refers to a molecule composed of monomers (amino acids) linearly linked by amide bonds (also known as peptide bonds). The term "polypeptide" refers to any chain or chains of two or more amino acids, and does not refer to a specific length of the product. As used herein the term "protein" is intended to encompass a molecule comprised of one or more polypeptides, which can in some instances be associated by bonds other than amide bonds. On the other hand, a protein can also be a single polypeptide chain. In this latter instance the single polypeptide chain can in some instances comprise two or more polypeptide subunits fused together to form a protein. The terms "polypeptide" and "protein" also refer to the products of post-expression modifications, including without limitation glycosylation, acetylation, phosphorylation, amidation, derivatization by known protecting/blocking groups, proteolytic cleavage, or modification by non-naturally occurring amino acids. A polypeptide or protein can be derived from a natural biological source or produced by recombinant technology, but is not necessarily translated from a designated nucleic acid sequence. It can be generated in any manner, including by chemical synthesis.

The term "polypeptide of interest" as used herein is used in its broadest sense to include any protein (either natural or recombinant), present in a mixture, for which purification is desired. Such polypeptides of interest include, without limitation, enzymes, hormones, growth factors, cytokines, immunoglobulins (e.g., antibodies), and/or any fusion proteins.

The term "production stage" of the cell culture refers to last stage of cell culture. During the production stage, cells will grow first and then followed with polypeptide production. The production stage is commonly referred to as "N" or last stage of cell culture manufacturing.

The terms "purifying," "separating," "isolating," or "recovering," as used interchangeably herein, refer to at least partially purifying or isolating (e.g., at least or about 5%, e.g., at least or about 10%, 15%, 20%, 25%, 30%, 40%, 45%, 50%, 55%, 60%, 65%, 70%, 75%, 80%, 85%, 90%, or at least or about 95% pure by weight) a recombinant protein from one or more other components present in the cell culture medium (e.g., mammalian cells or culture medium proteins) or one or more other components (e.g., DNA, RNA, or other proteins) present in a mammalian cell lysate. Typically, the degree of purity of the protein of interest is increased by removing (completely or partially) at least one impurity from the composition.

The terms "recombinantly expressed polypeptide" and "recombinant polypeptide" as used herein refer to a polypeptide expressed from a mammalian host cell that has been genetically engineered to express that polypeptide. The recombinantly expressed polypeptide can be identical or similar to polypeptides that are normally expressed in the mammalian host cell. The recombinantly expressed polypeptide can also foreign to the host cell, i.e. heterologous to peptides normally expressed in the mammalian host cell. Alternatively, the recombinantly expressed polypeptide can be chimeric in that portions of the polypeptide contain amino acid sequences that are identical or similar to polypeptides normally expressed in the mammalian host cell, while other portions are foreign to the host cell.

The term "seeding" as used herein refers to the process of providing a cell culture to a bioreactor or another vessel. The cells may have been propagated previously in another bioreactor or vessel. Alternatively, the cells may have been frozen and thawed immediately prior to providing them to the bioreactor or vessel. The term refers to any number of cells, including a single cell.

The term "shake flask" is meant a vessel (e.g., a sterile vessel) that can hold a volume of liquid culture medium that has at least one gas permeable surface. For example, a shake flask can be a cell culture flask, such as a T-flask, an Erlenmeyer flask, or any art-recognized modified version thereof.

'The term "titer" as used herein refers to the total amount of recombinantly expressed polypeptide or protein produced by a mammalian cell culture divided by a given amount of medium volume. Titer is typically expressed in units of milligrams of polypeptide or protein per milliliter of medium.

Various aspects of the disclosure are described in further detail in the following subsections.

Methods of the Invention

This In certain embodiments, this disclosure provides novel methods of increasing the viable cell density of an N−1 large-scale bioreactor cell culture, comprising culturing a host cell expressing a recombinant polypeptide of interest in a non-perfusion-based culture system, and wherein the viable cell density is increased to at least $5 \times 10^6$ cells/mL.

In certain embodiments, the disclosure provides novel methods for large-scale production of a recombinant polypeptide of interest, comprising: (1) culturing a host cell expressing a recombinant polypeptide of interest in an N−1 stage in a non-perfusion-based culture system, wherein the viable cell density is increased to at least $5 \times 10^6$ cells/mL; and (2) culturing the cells in an N production stage, which are inoculated from the N−1 cell culture in a non-perfusion culture system, in enriched media with high-seed density to at least $1.5 \times 10^6$ cells/mL.

Host Cells

Any mammalian cell or cell type susceptible to cell culture, and to expression of polypeptides, may be utilized in accordance with the present invention. Non-limiting examples of mammalian cells that may be used in accordance with the present invention include BALB/c mouse myeloma line (NSO/1, ECACC No: 85110503); human retinoblasts (PER.C6 (CruCell, Leiden, The Netherlands)); monkey kidney CV1 line transformed by SV40 (COS-7, ATCC CRL 1651); human embryonic kidney line (293 or 293 cells subcloned for growth in suspension culture, Graham et al., J. Gen Virol., 36:59 (1977)); baby hamster kidney cells (BHK, ATCC CCL 10); Chinese hamster ovary cells±DHFR (CHO, Urlaub and Chasin, Proc. Natl. Acad. Sci. USA, 77:4216 (1980)); mouse sertoli cells (TM4, Mather, Biol. Reprod., 23:243-251 (1980)); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL5 1); TRI cells (Mather et al., Annals N.Y. Acad. Sci., 383:44-68 (1982)); MRC 5 cells; FS4 cells; and a human hepatoma line (Hep G2). In one embodiment, the present invention is used in the culturing of and expression of polypeptides and proteins from CHO cell lines.

Additionally, any number of commercially and non-commercially available hybridoma cell lines that express polypeptides or proteins may be utilized in accordance with the present invention. One skilled in the art will appreciate that hybridoma cell lines might have different nutrition requirements and/or might require different culture conditions for optimal growth and polypeptide or protein expression, and will be able to modify conditions as needed.

As noted above, in many instances the cells will be selected or engineered to produce high levels of protein or polypeptide. Often, cells are genetically engineered to produce high levels of protein, for example by introduction of a gene encoding the protein or polypeptide of interest and/or by introduction of control elements that regulate expression of the gene (whether endogenous or introduced) encoding the polypeptide of interest.

Certain polypeptides may have detrimental effects on cell growth, cell viability or some other characteristic of the cells that ultimately limits production of the polypeptide or protein of interest in some way. Even amongst a population of cells of one particular type engineered to express a specific polypeptide, variability within the cellular population exists such that certain individual cells will grow better and/or produce more polypeptide of interest. In certain embodiments of the present invention, the cell line is empirically selected by the practitioner for robust growth under the particular conditions chosen for culturing the cells. In other embodiments, individual cells engineered to express a particular polypeptide are chosen for large-scale production based on cell growth, final cell density, percent cell viability, titer of the expressed polypeptide or any combination of these or any other conditions deemed important by the practitioner.

Fed-Batch Cell Culture Production

Typical procedures for producing a polypeptide of interest include batch cultures for seed expansion and fed-batch culture production stage. Batch seed culture processes traditionally comprise inoculating a large-scale production culture with a seed culture of a particular cell density, growing the cells under conditions conducive to cell growth and viability, and transferring the seed culture to next stage when the cells reach a specified cell density. Fed-batch culture procedures include an additional step or steps of supplementing the batch culture with nutrients and other components that are consumed during the growth of the cells. One of ordinary skill in the art will recognize that the present invention can be employed in any system in which cells are cultured including, but not limited to, batch, fed-batch and perfusion systems. In certain preferred embodiments of the present invention, the cells are grown in batch or fed-batch systems.

Enriched Media

The present invention provides enriched, chemically-defined media formulations that, when used in accordance with other culturing steps described herein, increase viable cell density of the host cells in N–1 culture and/or provide more nutrients in the production culture with high-seed density, relative to host cells cultured in non-enriched media. Enriched media formulations of the present invention that have been shown to have beneficial effects on cell growth or on production of polypeptide of interest include i) an increased amount of a carbon source and/or ii) increased nutrients relative to a standard culture media. Moreover, the carbon source can be: casein, lactate, dextrose, fructose, fructan, glucose, sucrose, lactose, maltose, acetate, glycerol, sorbitol, mannitol, saccharose, xylose, molasses, fucose, glucosamine, dextran, a fat, an oil, glycerol, sodium acetate, arabinose, soy protein, soluble protein, raffinose, amylose, starch, tryptone, yeast extract and combinations thereof, and the nutrients can be amino acids. The enriched media is enriched with feed media at 5%, at least 10%, at least 15%, or at least 20% with a carbon source and/or nutrients relative to non-enriched media. One of ordinary skill in the art will understand that the media formulations of the present invention encompass both defined and non-defined media.

An unexpected result of using enriched media, shown in Examples 1-3, is that host cells cultured in a batch method with enriched media during the N–1 culture stage show increased viable cell density relative to host cells cultured in a batch method with non-enriched media. Also, host cells cultured in a batch method with enriched media showed similar viable cell density and/or cell viability as host cell cultured in a fed-batch method without enriched media. Thus, host cells cultured in a batch method with enriched media can achieve similar results to host cells cultured in a perfusion or fed-batch system with non-enriched media.

Another unexpected result of using enriched media, shown in Examples 1-3, are that production cultures that were seeded from cells grown in a batch culture with enriched media had a similar titers for the polypeptide of interest as the production cultures that were seeded with cells from perfusion or fed-batch methods without enriched media. The conditions listed above may be used either singly or in various combinations with one another.

Any of these media formulations disclosed in the present invention may optionally be supplemented as necessary with hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, protein hydrolysates, or glucose or other energy source. In certain embodiments of the present invention, it may be beneficial to supplement the media with chemical inductants such as hexamethylene-bis (acetamide) ("HMBA") and sodium butyrate ("NaB"). These optional supplements may be added at the beginning of the culture or may be added at a later point in order to replenish depleted nutrients or for another reason. One of ordinary skill in the art will be aware of any desirable or necessary supplements that may be included in the disclosed media formulations.

Providing a Mammalian Cell Culture

Once a cell that expresses the polypeptide or protein of interest has been identified, the cell is propagated in culture by any of the variety of methods well-known to one of ordinary skill in the art. The cell expressing the polypeptide or protein of interest is typically propagated by growing it at a temperature and in a medium that is conducive to the survival, growth and viability of the cell. The initial culture volume can be of any size, but is often smaller than the culture volume of the production bioreactor used in the final production of the polypeptide or protein of interest, and frequently cells are passaged several times in bioreactors of increasing volume prior to seeding the production bioreactor. Once the cells have reached a specific viable cell density, the cells are grown in a bioreactor to further increase the number of viable cells. These bioreactors are referred to as N–1, N–2, N–3, and etc. "N" refers to the main production culture bioreactor, while the "N–1" means the bioreactor prior to the main production culture, and so forth.

The cell culture can be agitated or shaken to increase oxygenation of the medium and dispersion of nutrients to the cells. Alternatively or additionally, special sparging devices that are well known in the art can be used to increase and control oxygenation of the culture. In accordance with the present invention, one of ordinary skill in the art will understand that it can be beneficial to control or regulate certain internal conditions of the bioreactor, including but not limited to pH, temperature, oxygenation, etc.

The starting cell density in the N–3 bioreactor can be chosen by one of ordinary skill in the art. In accordance with the present invention, the starting cell density in the production bioreactor can be as low as $2\times10^4$ viable cells/mL. In certain embodiments of the present invention, starting cell densities in the N–3 bioreactor can range from $2\times10^4$, $2\times10^5$, $2\times10^6$, $5\times10^6$, $10\times10^6$ viable cells per mL and higher. Culturing the N–3 host cells with enriched media can lead to viable cell densities of at least $5\times10^6$ viable cells per mL to $5\times10^6$, $10\times10^6$, $15\times10^6$, $20\times10^6$, $25\times10^6$ or $30\times10^6$ viable cells per mL and higher.

The starting cell density in the N–2 bioreactor can be chosen by one of ordinary skill in the art. In accordance with the present invention, the starting cell density in the production bioreactor can be as low as $2\times10^4$ viable cells/mL. In certain embodiments of the present invention, starting cell densities in the N–2 bioreactor can range from about $2\times10^4$ viable cells per mL to about $2\times10^5$, $2\times10^6$, $5\times10^6$, $10\times10^6$ viable cells per mL and higher. Culturing the N–2 host cells with enriched media can lead to viable cell densities of at least $5\times10^6$ viable cells per mL to $10\times10^6$, $15\times10^6$, $20\times10^6$, $25\times10^6$ or $30\times10^6$ viable cells per mL and higher.

The starting cell density in the N–1 bioreactor can be chosen by one of ordinary skill in the art. In accordance with the present invention, the starting cell density in the production bioreactor can be as low as a single cell per culture volume. In certain embodiments of the present invention, starting cell densities in the production bioreactor can range from about $2\times10^4$ viable cells per mL to about $2\times10^5$, $2\times10^6$, $5\times10^6$, $10\times10^6$ viable cells per mL and higher. Culturing the N–1 host cells with enriched media can lead to viable cell densities of at least $5\times10^6$ viable cells per mL to about $5\times10^6$, $10\times10^6$, $15\times10^6$, $20\times10^6$, $25\times10^6$ or $30\times10^6$ viable cells per mL and higher.

The starting cell density in the N production bioreactor can be chosen by one of ordinary skill in the art. In accordance with the present invention, the starting cell density in the N production bioreactor can be as low as $1\times10^6$ cells/mL. In certain embodiments of the present invention, starting cell densities in the production bioreactor can range from about $1\times10^6$ viable cells per mL to about $2\times10^6$, $5\times10^6$, $10\times10^6$ viable cells per mL and higher. Culturing the host cells with enriched media can lead to viable cell densities of at least $1\times10^6$ viable cells per mL to about $2\times10^6$, $5\times10^6$, $10\times10^6$, $15\times10^6$, $20\times10^6$, $25\times10^6$ or $30\times10^6$ viable cells per mL and higher.

Generally, cell cultures of N–1 may be grown to a desired density before seeding the next production bioreactor. It is preferred that most of the cells remain alive prior to seeding, although total or near total viability is not required. In one embodiment of the present invention, the cells may be removed from the supernatant, for example, by low-speed centrifugation. It may also be desirable to wash the removed cells with a medium before seeding the next bioreactor to remove any unwanted metabolic waste products or medium components. The medium may be the medium in which the cells were previously grown or it may be a different medium or a washing solution selected by the practitioner of the present invention.

The cells of N–1 may then be diluted to an appropriate density for seeding the production bioreactor. In a certain embodiment of the present invention, the cells are diluted into the same medium that will be used in the production bioreactor. Alternatively, the cells can be diluted into another medium or solution, depending on the needs and desires of the practitioner of the present invention or to accommodate particular requirements of the cells themselves, for example, if they are to be stored for a short period of time prior to seeding the production bioreactor.

In accordance with the present invention, the production bioreactor can be any volume that is appropriate for large-scale production of polypeptides or proteins. In a certain embodiment, the volume of the production bioreactor is at least 500 liters. In other embodiments, the volume of the production bioreactor is 1,000, 2,500, 5,000, 8000, 10,000, 15,000, or 20,000 liters or more, or any volume in between. One of ordinary skill in the art will be aware of and will be able to choose a suitable bioreactor for use in practicing the present invention. The production bioreactor may be constructed of any material that is conducive to cell growth and viability that does not interfere with expression or stability of the produced polypeptide or protein.

In certain embodiments of the present invention, the production stage comprises enriched media as relative to non-enriched media. For example, the media is enriched by feed media at least 5%, at least 10%, at least 15%, or at least 20% relative to non-enriched media. In certain embodiments, the enriched media comprises an increased amount of a carbon source (e.g., glucose). In certain embodiments, the enriched media comprises an increased amount of nutrients (e.g., amino acids). In certain embodiments, the enriched media comprises an increased amount of a carbon source and nutrients.

The temperature of the cell culture at the N–1 stage or the production stage will be selected based primarily on the range of temperatures at which the cell culture remains viable. In general, most mammalian cells grow well within a range of about 25° C. to 42° C. Preferably, mammalian cells grow well within the range of about 35° C. to 40° C. Those of ordinary skill in the art will be able to select appropriate temperature or temperatures in which to grow cells, depending on the needs of the cells and the production requirements of the practitioner. Optionally, the temperature is maintained at a single, constant temperature. Optionally, the temperature is maintained within a range of temperatures. For example, the temperature may be steadily increased or decreased. Alternatively, the temperature may be increased or decreased by discrete amounts at various times. One of ordinary skill in the art will be able to determine whether a single or multiple temperatures should be used, and whether the temperature should be adjusted steadily or by discrete amounts.

The cells at the N–1 stage or the production stage may be grown for a greater or lesser amount of time, depending on the needs of the practitioner and the requirement of the cells themselves. In one embodiment, the cells are grown for a period of time sufficient to achieve a viable cell density that is a given percentage of the maximal viable cell density that the cells would eventually reach if allowed to grow undisturbed. The cells are allowed to grow for a defined period of time. For example, depending on the starting concentration of the cell culture, the temperature at which the cells are grown, and the intrinsic growth rate of the cells, the cells may be grown for 0, 1, 2, 3, 4, 5, 6, 7, 8, 9, 10, 11, 12, 13, 14, 15, 16, 17, 18, 19, 20 or more days. The practitioner of the present invention will be able to choose the duration of growth depending on the polypeptide production requirements and the needs of the cells themselves.

Monitoring Culture Conditions

In certain embodiments of the present invention, particular conditions of the growing cell culture are monitored. Monitoring cell culture conditions allows for the determination of whether the cell culture is producing recombinant polypeptide or protein at suboptimal levels or whether the culture is about to enter into a suboptimal production stage.

As non-limiting examples, it may be beneficial or necessary to monitor temperature, pH, cell density, cell viability, integrated viable cell density, lactate levels, ammonium levels, osmolarity, or titer of the expressed polypeptide or protein. Numerous techniques are well known in the art that will allow one of ordinary skill in the art to measure these conditions. For example, cell density may be measured using a hemacytometer, a Coulter counter (Vi-Cell), or Cell density examination (CEDEX). Viable cell density may be determined by staining a culture sample with Trypan blue. Since only dead cells take up the Trypan blue, viable cell density can be determined by counting the total number of cells, dividing the number of cells that take up the dye by the total number of cells, and taking the reciprocal. HPLC can be used to determine the levels of lactate, ammonium or the expressed polypeptide or protein. Alternatively, the level of the expressed polypeptide or protein can be determined by standard molecular biology techniques such as coomassie staining of SDS-PAGE gels, Western blotting, Bradford assays, Lowry assays, Biuret assays, and UV absorbance. It may also be beneficial or necessary to monitor the post-translational modifications of the expressed polypeptide or protein, including phosphorylation and glycosylation.

Isolation of Expressed Polypeptide

In general, it will typically be desirable to isolate and/or purify proteins or polypeptides expressed according to the present invention. In one embodiment, the expressed polypeptide or protein is secreted into the medium and thus cells and other solids may be removed, as by centrifugation or filtering for example, as a first step in the purification process. This embodiment is particularly useful when used in accordance with the present invention, since the methods and compositions described herein result in increased cell viability. As a result, fewer cells die during the culture process, and fewer proteolytic enzymes are released into the medium which can potentially decrease the yield of the expressed polypeptide or protein.

Recombinant Polypeptides

The methods of the present invention can be used for large-scale production of any recombinant polypeptides of interest, including therapeutic antibodies. Non-limiting examples of recombinant polypeptides that can be produced by the methods provided herein include antibodies (including intact immunoglobulins or antibody fragments), enzymes (e.g., a galactosidase), proteins (e.g., human erythropoietin, tumor necrosis factor (TNF), or an interferon alpha or beta), cellular receptors (e.g., EGFR) or immunogenic or antigenic proteins or protein fragments (e.g., proteins for use in a vaccine). Antibodies within the scope of the present invention include, but are not limited to: anti-HER2 antibodies including Trastuzumab (HERCEPTIN®) (Carter et al., *Proc. Natl. Acad. Sci. USA,* 89:4285-4289 (1992); anti-HER3 antibodies; anti-HER4 antibodies; U.S. Pat. No. 5,725,856); anti-CD20 antibodies such as chimeric anti-CD20 "C2B8" as in U.S. Pat. No. 5,736,137 (RITUXAN®), a chimeric or humanized variant of the 2H7 antibody as in U.S. Pat. No. 5,721,108B1, or Tositumomab (BEXXAR®); anti-IL-8 (St John et al., *Chest,* 103:932 (1993), and International Publication No. WO 95/23865); anti-VEGF antibodies including humanized and/or affinity matured anti-VEGF antibodies such as the humanized anti-VEGF antibody huA4.6.1 AVASTIN® (Kim et al., *Growth Factors,* 7:53-64 (1992), International Publication No. WO 96/30046, and WO 98/45331, published Oct. 15, 1998); anti-PSCA antibodies (WO01/40309); anti-CD40 antibodies, including S2C6 and humanized variants thereof (WO00/75348); anti-CD11a (U.S. Pat. No. 5,622,700, WO 98/23761, Steppe et al., *Transplant Intl.* 4:3-7 (1991), and Hourmant et al., *Transplantation* 58:377-380 (1994)); anti-IgE (Presta et al., *J. Immunol.* 151:2623-2632 (1993), and International Publication No. WO 95/19181); anti-CD18 (U.S. Pat. No. 5,622,700, issued Apr. 22, 1997, or as in WO 97/26912, published Jul. 31, 1997); anti-IgE (including E25, E26 and E27; U.S. Pat. No. 5,714,338, issued Feb. 3, 1998 or U.S. Pat. No. 5,091,313, issued Feb. 25, 1992, WO 93/04173 published Mar. 4, 1993, or International Application No. PCT/US98/13410 filed Jun. 30, 1998, U.S. Pat. No. 5,714,338); anti-Apo-2 receptor antibody (WO 98/51793 published Nov. 19, 1998); anti-TNF-α antibodies including cA2 (REMICADE®), CDP571 and MAK-195 (See, U.S. Pat. No. 5,672,347 issued Sep. 30, 1997, Lorenz et al., *J. Immunol.* 156 (4): 1646-1653 (1996), and Dhainaut et al., *Crit. Care Med.* 23 (9): 1461-1469 (1995)); anti-Tissue Factor (TF) (European Patent No. 0 420 937 B1 granted Nov. 9, 1994); anti-human $\alpha_4\beta_7$ integrin (WO 98/06248 published Feb. 19, 1998); anti-EGFR (chimerized or humanized 225 antibody as in WO 96/40210 published Dec. 19, 1996); anti-CD3 antibodies such as OKT3 (U.S. Pat. No. 4,515,893 issued May 7, 1985); anti-CD25 or anti-tac antibodies such as CH1-621 (SIMULECT®) and (ZENA-PAX®) (See U.S. Pat. No. 5,693,762 issued Dec. 2, 1997); anti-CD4 antibodies such as the cM-7412 antibody (Choy et al., *Arthritis Rheum* 39 (1): 52-56 (1996)); anti-CD52 antibodies such as CAMPATH-1H (Riechmann et al., *Nature* 332:323-337 (1988)); anti-Fc receptor antibodies such as the M22 antibody directed against FcγRI as in Graziano et al., *J. Immunol.* 155 (10): 4996-5002 (1995); anti-carcinoembryonic antigen (CEA) antibodies such as hMN-14 (Sharkey et al., *Cancer Res.* 55 (23 Suppl): 5935s-5945s (1995); antibodies directed against breast epithelial cells including huBrE-3, hu-Mc 3 and CHL6 (Ceriani et al., *Cancer Res.* 55 (23): 5852s-5856s (1995); and Richman et al., *Cancer Res.* 55 (23 Supp): 5916s-5920s (1995)); antibodies that bind to colon carcinoma cells such as C242 (Litton et al., *Eur J. Immunol.* 26 (1): 1-9 (1996)); anti-CD38 antibodies, e.g. AT 13/5 (Ellis et al., *J. Immunol.* 155 (2): 925-937 (1995)); anti-CD33 antibodies such as Hu M195 (Jurcic et al., *Cancer Res* 55 (23 Suppl): 5908s-5910s (1995) and CMA-676 or CDP771; anti-CD22 antibodies such as LL2 or LymphoCide (Juweid et al., *Cancer Res* 55 (23 Suppl): 5899s-5907s (1995)); anti-EpCAM antibodies such as 17-1A (PANOREX®); anti-GpIIb/IIIa antibodies such as abciximab or c7E3 Fab (REOPRO®); anti-RSV antibodies such as MEDI-493 (SYNAGIS®); anti-CMV antibodies such as PROTOVIR®; anti-HIV antibodies such as PRO542; anti-hepatitis antibodies such as the anti-Hep B antibody OSTAVIR®; anti-CA 125 antibody OvaRex; anti-idiotypic GD3 epitope antibody BEC2; anti-$\alpha v \beta 3$ antibody VITAXIN®; anti-human renal cell carcinoma antibody such as ch-G250; ING-1; anti-human 17-1A antibody (3622W94); anti-human colorectal tumor antibody (A33); anti-human melanoma antibody R24 directed against GD3 ganglioside; anti-human squamous-cell carcinoma (SF-25); anti-human leukocyte antigen (HLA) antibodies such as Smart ID10; anti-PD-1 antibodies; anti-PD-L1 antibodies; anti-LAG-3 antibodies; anti-GITR antibodies; anti-TIGIT antibodies; anti-CXCR4 antibodies; anti-CD73 antibodies; and the anti-HLA DR antibody Oncolym (Lym-1).

The foregoing description is to be understood as being representative only and is not intended to be limiting. Alternative methods and materials for implementing the invention and also additional applications will be apparent to one of skill in the art, and are intended to be included within the accompanying claims.

EXAMPLES

Cell Lines and Media

Three different CHO cell lines producing three different monoclonal antibodies or polypeptides were used in these experiments. The seed, basal and feed media used were chemically-defined.

N–1 Seed Cultures

For batch and fed-batch N–1 cultures, cells were grown either in 250 ml shake flasks with an initial volume of 80-100 ml or 2 L shake flasks with an initial volume of 1000 ml. A shaking speed of 150 rpm on an orbital shaker with 25 mm throw distance was used. The incubator settings were at constant temperature of 36.5° C. and $CO_2$ was controlled at 5%. For the batch N–1 cultures, the seed media were either without enrichment, or with glucose enrichment, or with glucose and nutrient enrichments. No feed was added to the batch N–1 cultures. For the fed-batch N–1 cultures, the seed medium was fed daily from day 3 on.

Perfusion N–1 cultures involved growing the cells in 10 L cell bags with an initial volume of 5 L. Rocking speed was controlled at 28 rpm and rocking angle was set at 7°. $CO_2$ was controlled at 4% between day 0 and 1 and then turned off. An auxiliary ATF-2 (Repligen) was connected to the cell bag to perfuse the culture. Fresh culture medium (1× concentrated) is continuously added while old culture medium is continuously removed at the same rate according to the schedule: 0.5 VVD D2-4, increased to 1.0 VVD D4-5, and final increase to 2.0 VVD D5-6.

Production Cultures

The fed-batch production bioreactors were performed in 5 L Sartorius bioreactors with 3.3 L initial working volume.

Analyses

Viable cell density (VCD) and cell viability were measured off-line using a Vi-Cell automated cell counter (Beckman Coulter). Culture samples were also analyzed off-line using a Cedex Bio HT (Roche) to monitor glucose, glutamine, glutamate, lactate, and ammonium. For bioreactor cultures, pH, $pCO_2$, $pO_2$ were also measured offline using a BioProfile pHOX (Nova Biomedical). A Protein A UPLC method was used to measure protein titer, which were reported as normalized values.

Size exclusion chromatography (SEC) for high molecular weight (HMW) was performed using a Tosoh TSK G3000SW$_{xl}$ column, 7.8×30 cm, 5 um, with an isocratic gradient monitored at 280 nm on a Waters Alliance HPLC system (Milford, MA) equipped with a temperature controlled autosampler and Waters 2996 PDA detector.

Charge Variants were assayed by Imaged Capillary Isoelectric Focusing (iCIEF), which was performed on a Protein Simple iCE3 instrument with an Alcott 720NV autosampler (San Jose, CA). Samples were mixed with appropriate pI markers, ampholytes, and urea and injected into a fluorocarbon coated capillary cartridge. A high voltage was applied and the charged variants migrated to their respective pI. A UV camera captured the image at 280 nM. The main peak was identified and the peaks that migrated into the acidic range and basic range were summed, quantitated, and reported as relative percent area.

N-Glycans analysis was performed using a commercially available kit from Prozyme, GlykoPrep® Rapid N-Glycan Preparation with 2-AB (Hayward, CA). The free oligosaccharides were profiled using an Acquity UPLC Glycan BEH Amide, 130 Å, 1.7 µm, 2.1×10 mm column (Milford, MA) on a Waters Acquity H-Class system (Milford, MA) equipped with a temperature controlled autosampler and fluorescence detector.

Example 1

Cell Line A: N–1 Seed Cultures

For Cell Line A, the N–1 cultures were grown in batch, batch with glucose enrichment, batch with glucose and nutrient enrichments, fed-batch or perfusion mode. The batch N–1 culture reached peak VCD of only $15 \times 10^6$ cells per mL and failed to maintain high cell viability near the end of the culture period (FIG. 1A). In contrast, the batch N–1 culture with glucose enrichment reached VCD of $17 \times 10^6$ cells per mL and maintained >99% cell viability (FIG. 1A). Similarly, both the fed-batch N–1 and batch N–1 with glucose and nutrient enrichments grew to $>20 \times 10^6$ cells per mL on day 6 and viabilities were maintained at >99% (FIGS. 1A and 1B). The cells in perfusion N–1 culture grew to $44 \times 10^6$ cells per mL on day 6 and viability was >99% (FIGS. 1A and 1B).

Cell Line A for Production of Polypeptide-1: High Density Fed-Batch Production Cultures For Cell Line A, high density fed-batch production cultures were initiated using seeds grown in batch with enriched glucose, batch with enriched glucose and nutrients, fed-batch or perfusion cultures.

The N production culture was inoculated at high seed density of $5 \times 10^6$ cells per mL for 14 days. Daily feed was started on day 2 at a feeding volume of 3.5% of culture volume. Dissolved oxygen (DO) was maintained at 40% and pH was controlled between 6.8 and 7.6. Temperature was initially maintained at 36.5° C. and shifted to 34° C. on day 4.

Figure 2B:
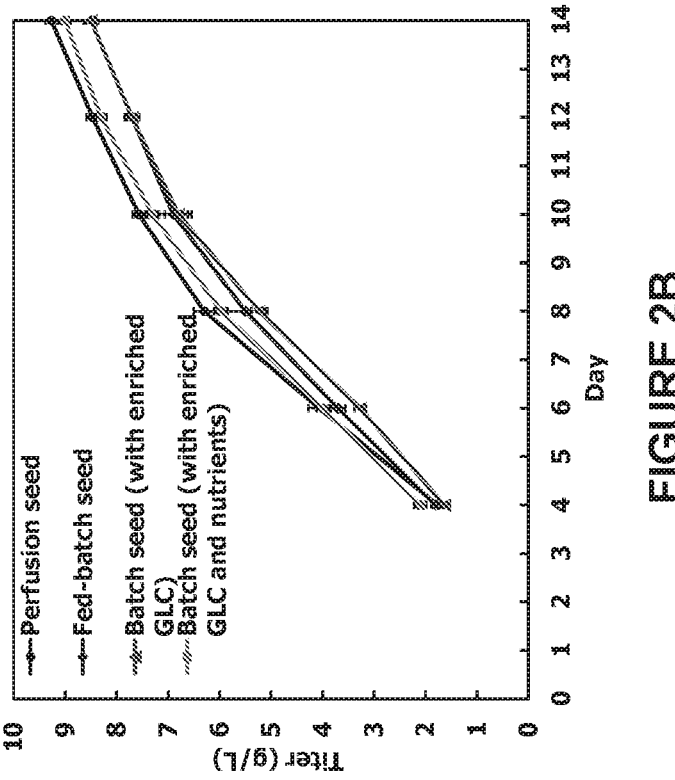
FIGS. 2A-2C.
Figure 2A:
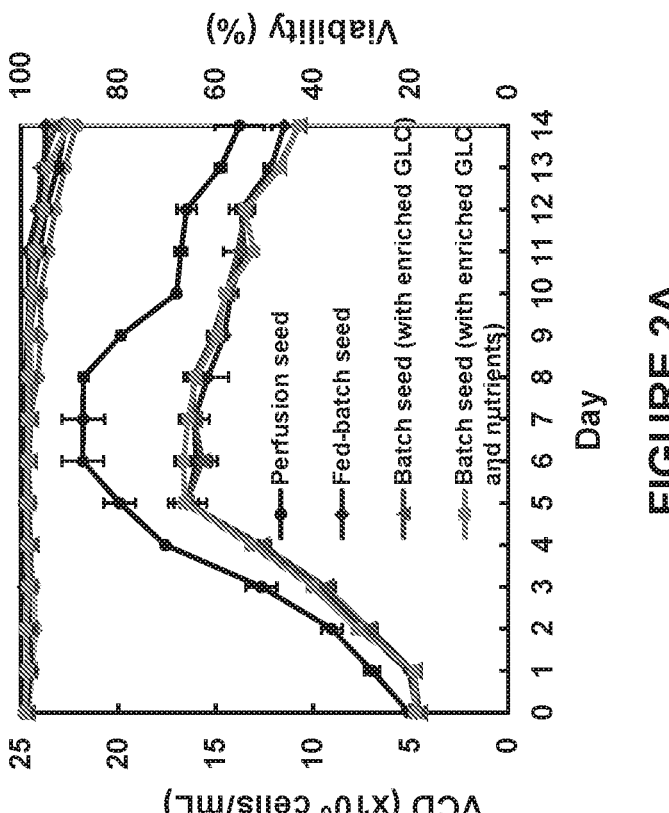
Figure 2C:
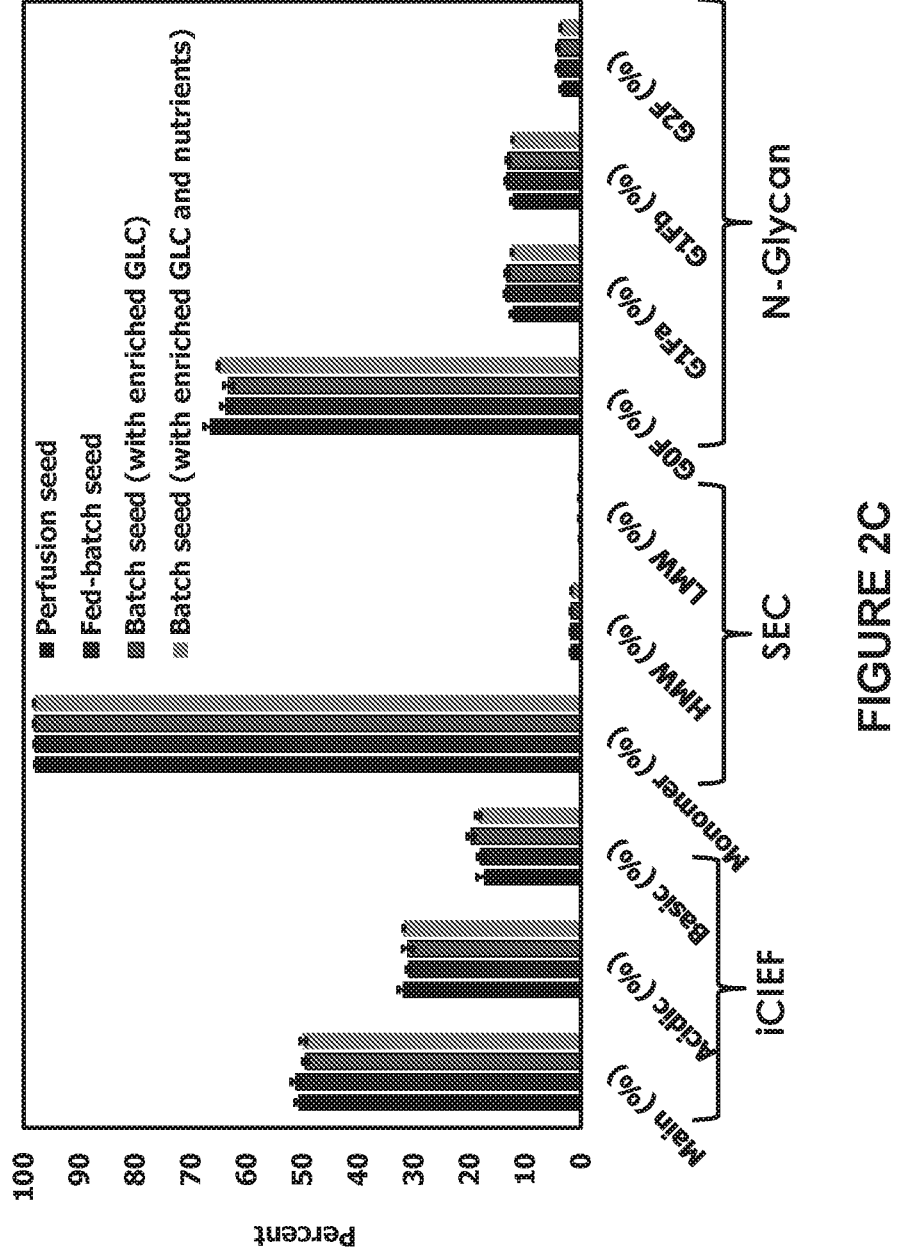

FIG. 2A demonstrates that all production cultures maintained >90% cell viability over the entire culture period. The perfusion seed culture had a maximum viable cell density of $22 \times 10^6$ cells per mL compared to $17 \times 10^6$ cells per mL for fed-batch seed culture and batch seed cultures with either enriched glucose or enriched glucose and nutrients (FIG. 2A). The titer for the polypeptide-1 from the perfusion seed culture was approximately 9.3 g/L, while the fed-batch seed culture had a titer of approximately 9 g/L (FIG. 2B). The titer of the polypeptide of interest from the batch seed enriched with either glucose or glucose and nutrients was approximately 8.5 g/L and 9 g/L, respectively. FIG. 2C shows that quality attributes such as iCIEF, SEC, and N-glycan were similar for all N production conditions regardless of different N–1 seeds.

Example 2

Cell Line B: N–1 Seed Cultures

Figures 3A, 3B:
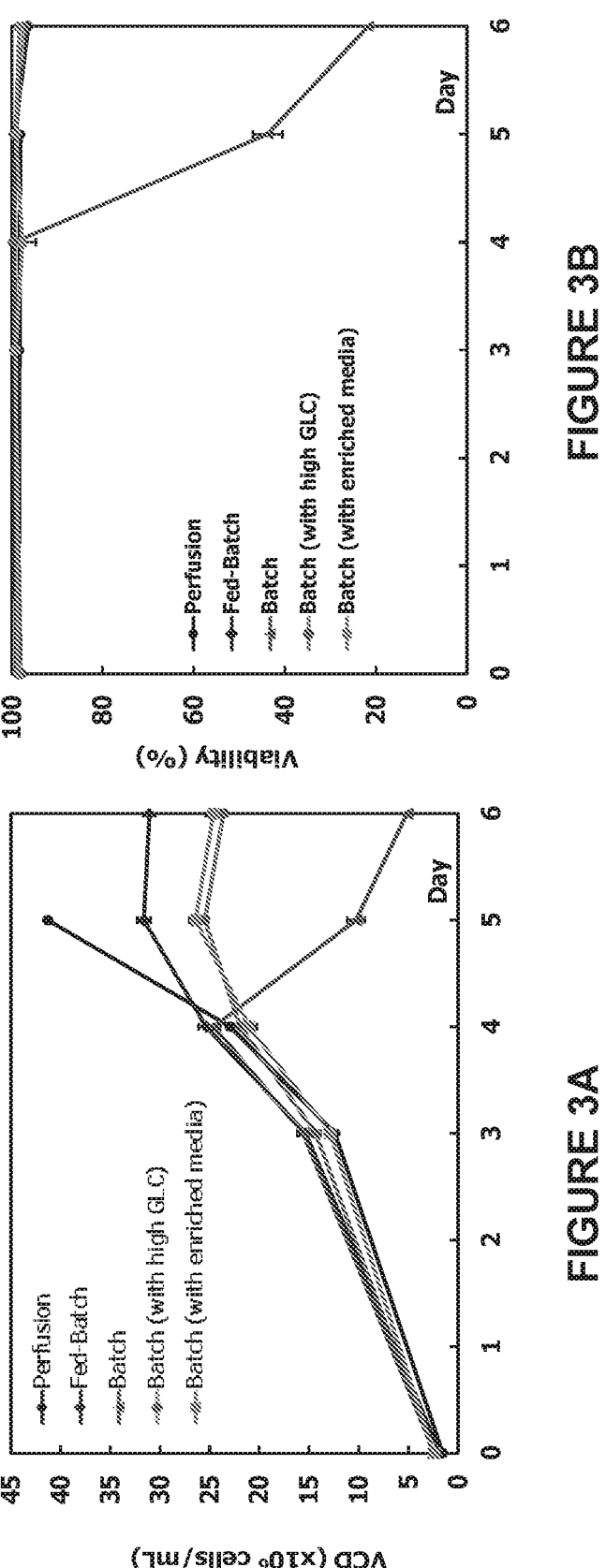
FIGS. 3A and 3B.

For Cell Line B, the N–1 cultures were grown in batch, batch with glucose enrichment, batch with glucose and nutrient enrichments, fed-batch or perfusion mode. The batch N–1 culture reached peak VCD of only $24.5 \times 10^6$ cells per mL and failed to maintain high viability (FIGS. 3A and 3B). In contrast, the batch N–1 cultures enriched with glucose alone or enriched with both glucose and nutrients reached $>25.5 \times 10^6$ viable cells per mL and maintained $>99\%$ cell viability (FIGS. 3A and 3B). Similarly, the fed-batch N–1 cultures grew to $\geq 30 \times 10^6$ viable cells per mL on day 5 and viabilities were maintained at $>99\%$ (FIGS. 3A and 3B). The cells in perfusion N–1 culture grew to $41 \times 10^6$ cells per mL on day 5 and viability was $>99\%$ (FIGS. 3A and 3B).

Cell Line B for production of polypeptide-2: High Density Fed-Batch Production Cultures For Cell Line B, high density fed-batch production cultures were initiated using seeds grown in batch, batch with enriched glucose and nutrients, fed-batch or perfusion cultures.

The production culture was inoculated at high seed density of $3 \times 10^6$ cells per mL for 14 days. Daily feed was started on day 2 at a feeding volume of 3.1% of culture volume. Dissolved oxygen (DO) was maintained at 40% and pH was controlled between 6.7 and 7.6. Temperature was maintained at 36.5° C.

Figures 4A, 4B:
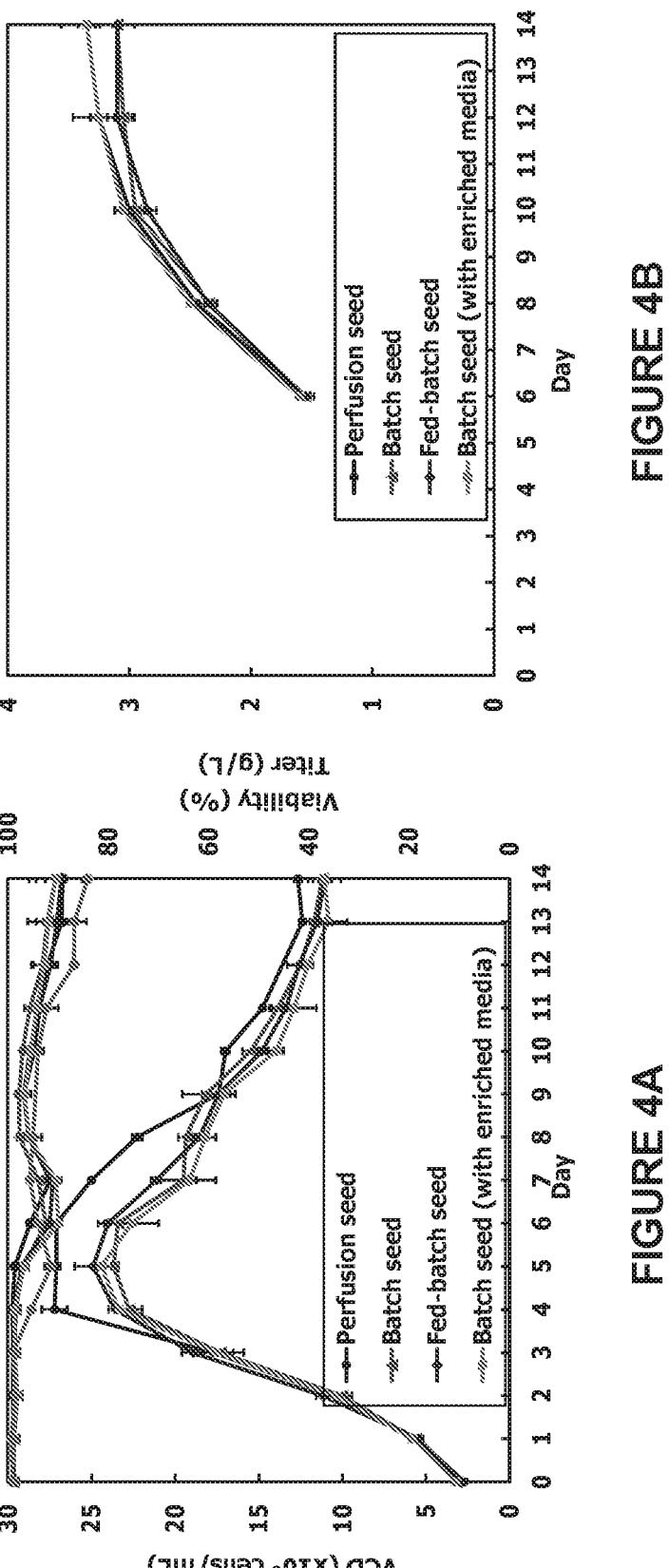
FIGS. 4A-4C.
Figure 4C:
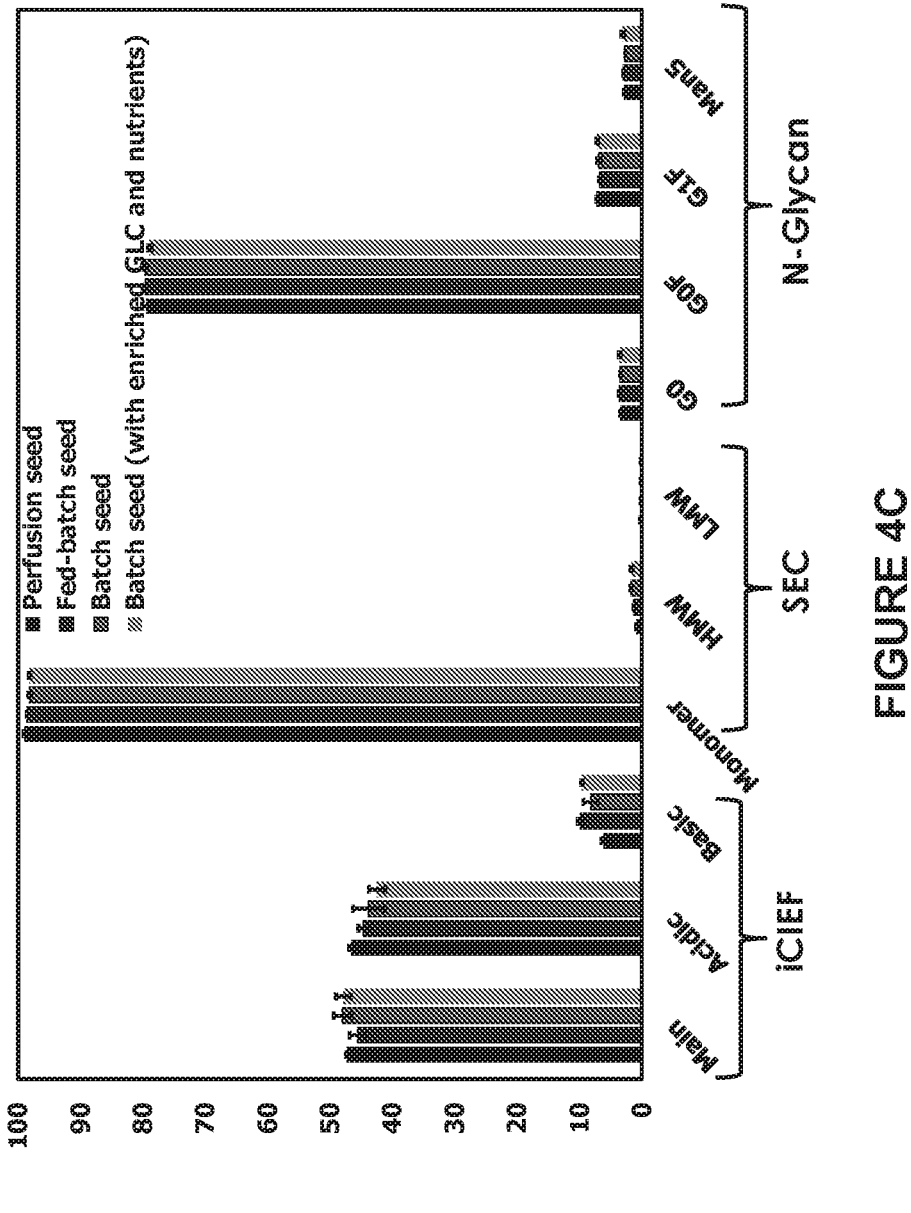

FIG. 4A demonstrates that all production cultures maintained $>90\%$ cell viability over the entire culture period. The perfusion seed culture had a maximum viable cell density approximately $26 \times 10^6$ cells per mL compared to only approximately $24 \times 10^6$ cells per mL for fed-batch and batch seed cultures with either enriched glucose or enriched glucose and nutrients (FIG. 4A). The titer of the polypeptide of interest from the perfusion and batch seed (with enriched glucose and nutrients) cultures was approximately 3.2 g/L, while the batch and fed-batch seed cultures had a titer of approximately 3 g/L (FIG. 4B). FIG. 4C shows that quality attributes such as iCIEF, SEC, and N-glycan were similar for all N production conditions regardless of different N–1 seeds.

Example 3

Cell Line C: N–1 Seed Cultures

Figures 5A, 5B:
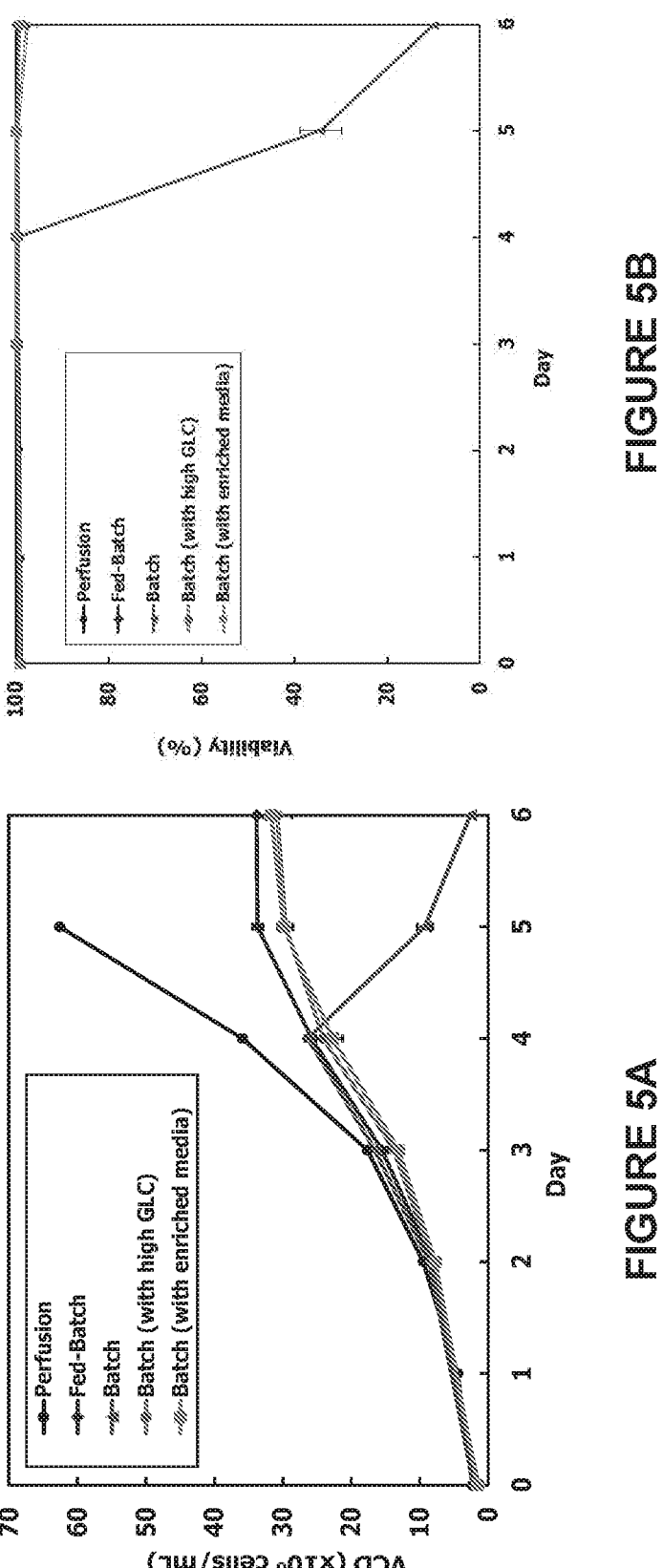
FIGS. 5A and 5B.

For Cell Line C, the N–1 cultures were grown in batch, batch with glucose enrichment, batch with glucose and nutrient enrichments, fed-batch or perfusion mode. The batch N–1 culture reached peak VCD of only $26 \times 10^6$ cells per mL and failed to maintain high viability (FIGS. 5A and 5B). In contrast, the batch N–1 cultures enriched with glucose alone or enriched with both glucose and nutrients reached $>30 \times 10^6$ viable cells per mL and maintained $>99\%$ cell viability (FIGS. 5A and 5B). Similarly, the fed-batch N–1 cultures grew to $\geq 33 \times 10^6$ viable cells per mL on day 5 and viabilities were maintained at $>99\%$ (FIGS. 5A and 5B). The cells in perfusion N–1 culture grew to $62 \times 10^6$ cells per mL on day 5 and viability was $>99\%$ (FIGS. 5A and 5B).

Cell Line C for Production of Polypeptide-3 (Experiment 1): High Density Fed-Batch Production Cultures Using Fed-Batch or Batch with Enriched Glucose and Nutrients Seeds For Cell Line C, high density fed-batch production cultures were initiated using seeds grown in fed-batch or batch with enriched glucose and nutrients culture.

The production culture was initiated at high seed density of $6 \times 10^6$ cells per mL for 14 days. Daily feed was started on day 2 at a feeding volume of 5% of culture volume D2-10 and then 3.3% of initial culture volume D11-13. Feeding was performed twice a day at half the amount indicated. Dissolved oxygen (DO) was maintained at 40% and pH was controlled between 6.8 and 7.3. Temperature was initially maintained at 36.5° C. and shifted to 33° C. on day 6.

Figures 6A, 6B:
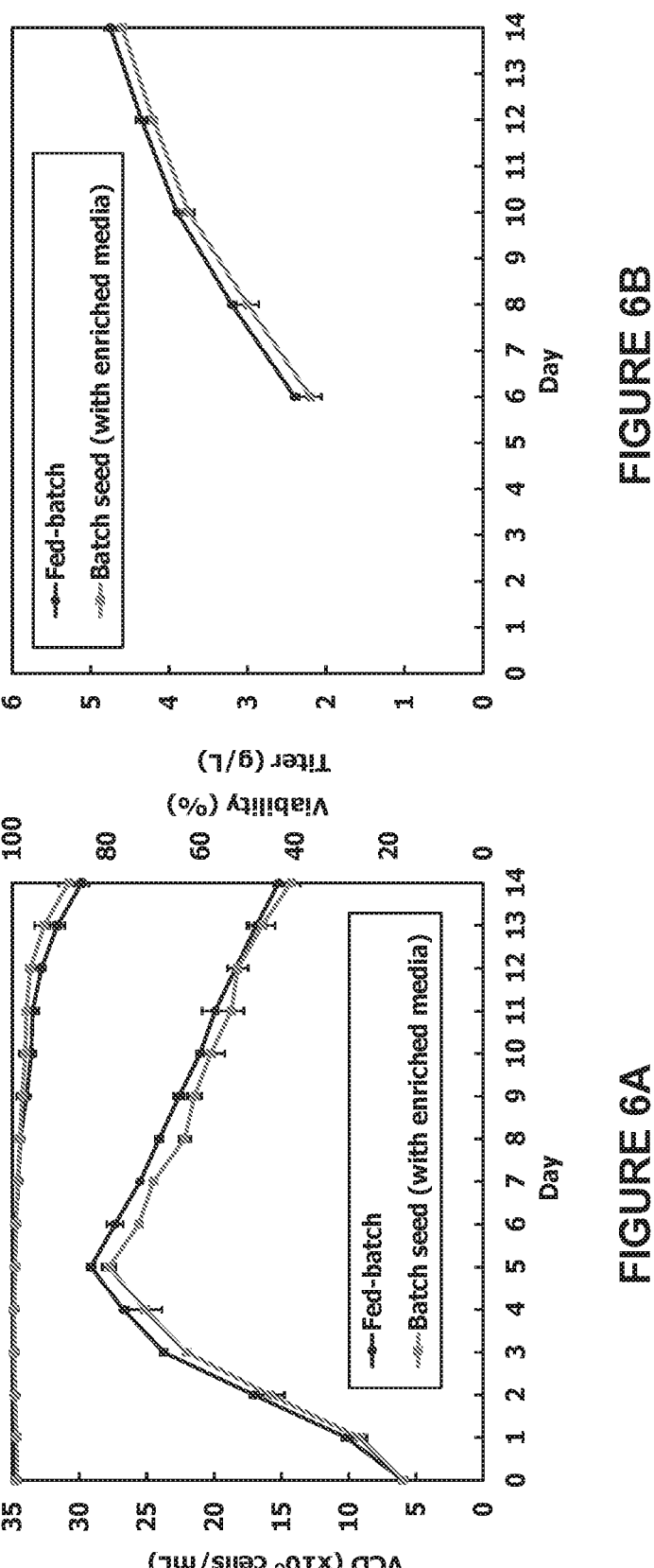
FIGS. 6A-6C.
Figure 6C:
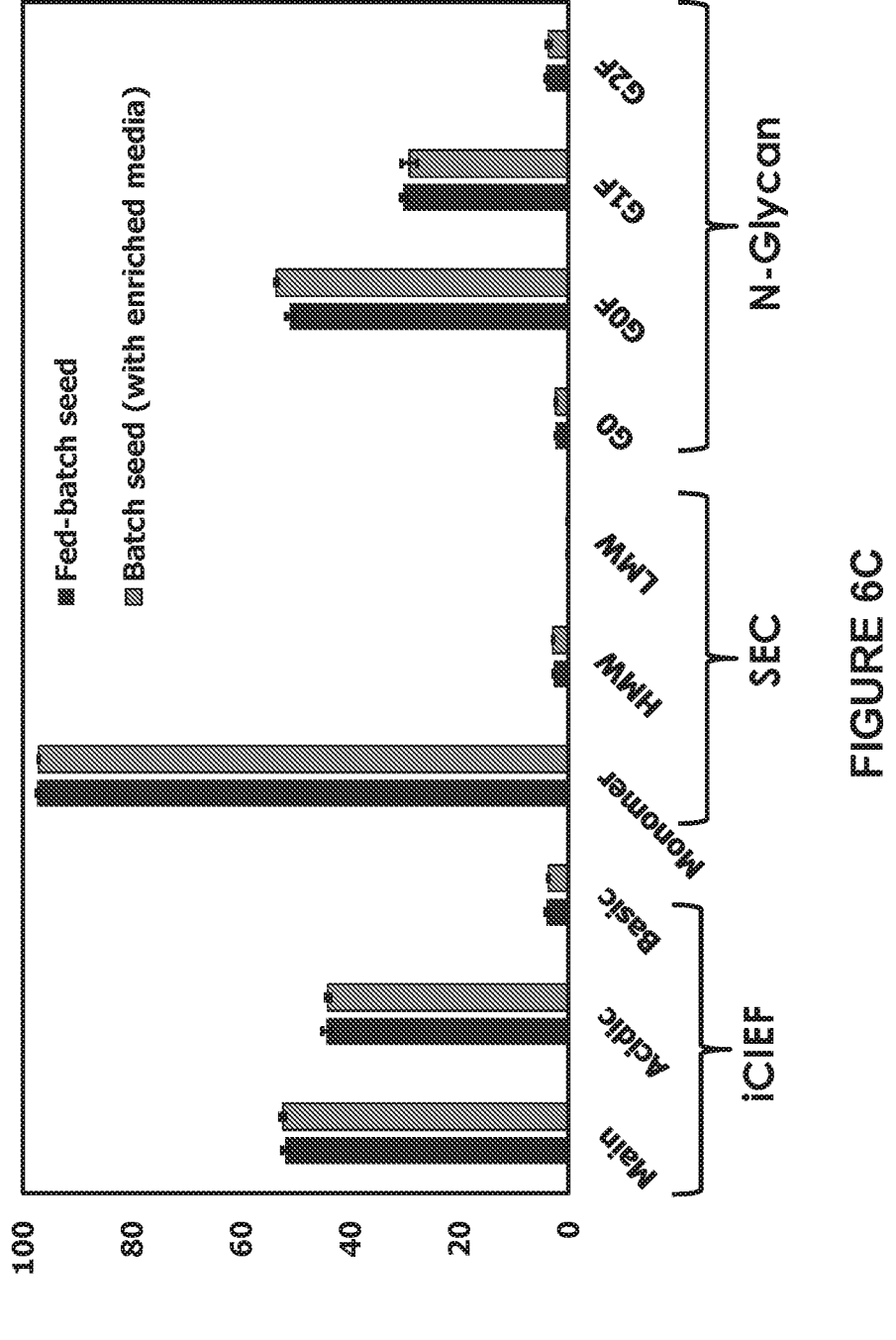

FIG. 6A demonstrates that all production cultures maintained $>80\%$ cell viability over the entire culture period. The fed-batch seed and batch (with enriched glucose and nutrients) seed cultures had a maximum viable cell density approximately $27 \times 10^6$ cells per mL (FIG. 6A). The titer of the polypeptide of interest from the fed-batch and batch (with enriched glucose and nutrients) seed cultures was approximately 4.3 g/L (FIG. 6B). FIG. 6C shows that quality attributes such as iCIEF, SEC, and N-glycan were similar for all N production conditions regardless of different N–1 seeds.

Cell Line C for Production of Polypeptide-3 (Experiment 2): High Density Fed-Batch Production Cultures Using Fed-Batch or Perfusion Seeds For Cell Line C, high density fed-batch production cultures were initiated using seeds grown in fed-batch or perfusion culture.

The production culture was initiated at high seed density of $6 \times 10^6$ cells per mL for 14 days. Daily feed was started on day 1 at a feeding volume of 3.7% of culture volume. Dissolved oxygen (DO) was maintained at 40% and pH was controlled between 6.8 and 7.3. Temperature was initially maintained at 36.5° C. and shifted to 33° C. on day 6.

Figure 7C:
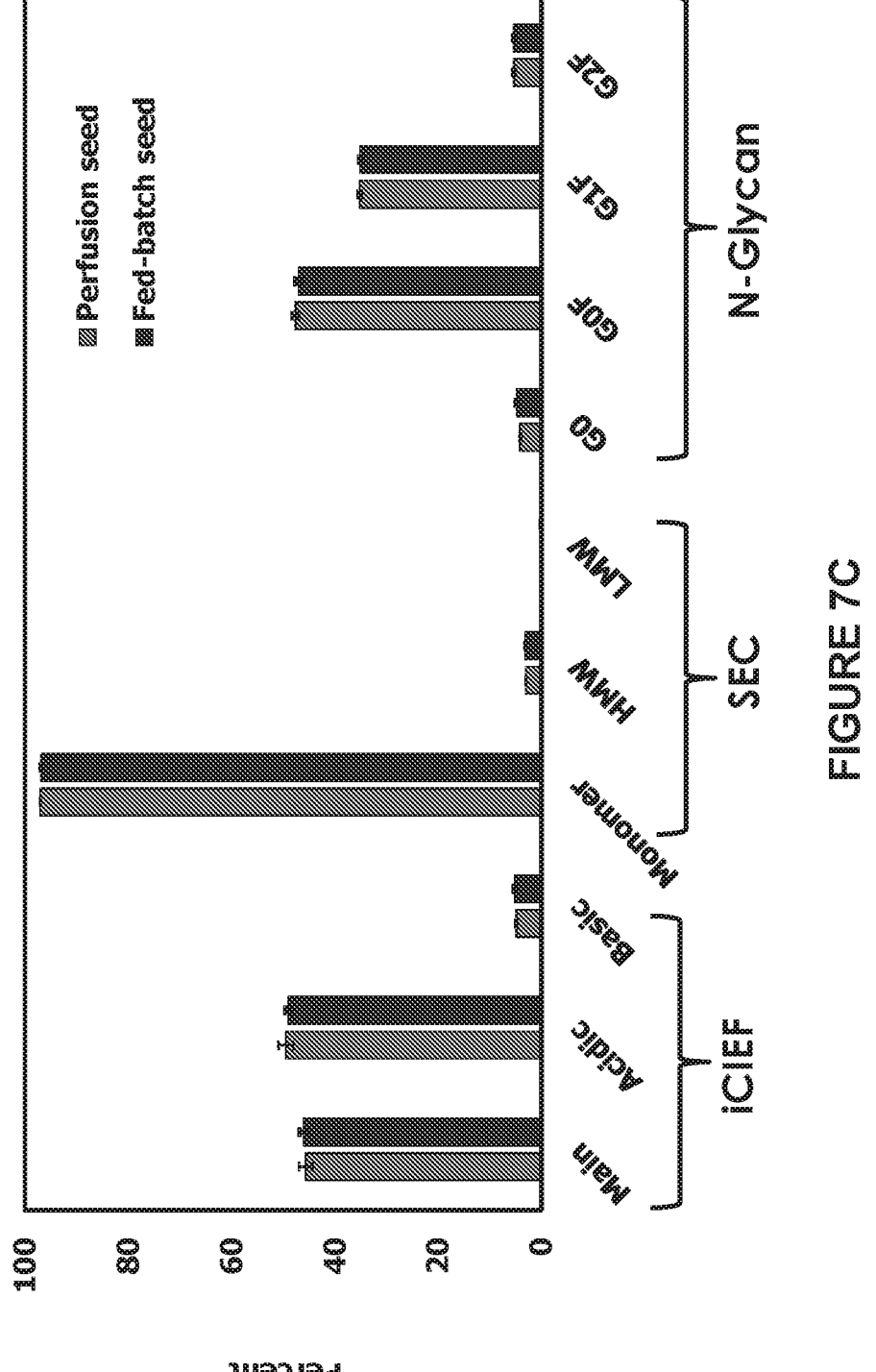

FIG. 7A demonstrates that all production cultures maintained $>80\%$ cell viability over the entire culture period. The perfusion seed culture had a maximum viable cell density of approximately $33 \times 10^6$ cells per mL, while the fed-batch seed culture had a maximum viable cell density approximately $30 \times 10^6$ cells per mL (FIG. 7A). The titer of the polypeptide of interest from the perfusion and fed-batch seed cultures was approximately 7 g/L (FIG. 7B). FIG. 7C shows that quality attributes such as iCIEF, SEC, and N-glycan were similar for all N production conditions regardless of different N–1 seeds.

Example 4

Figures 8A, 8B:
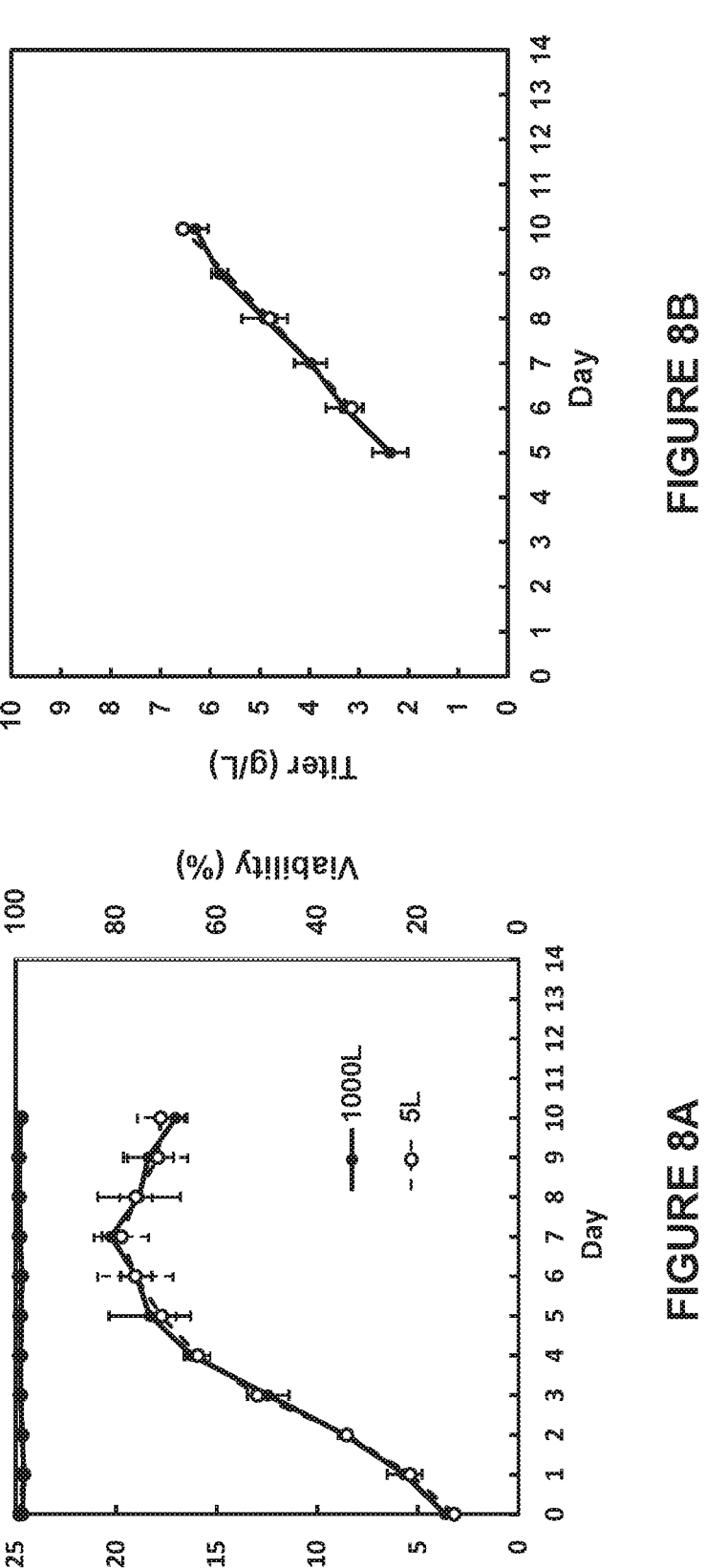
FIGS. 8A-8C.
Figure 8C:
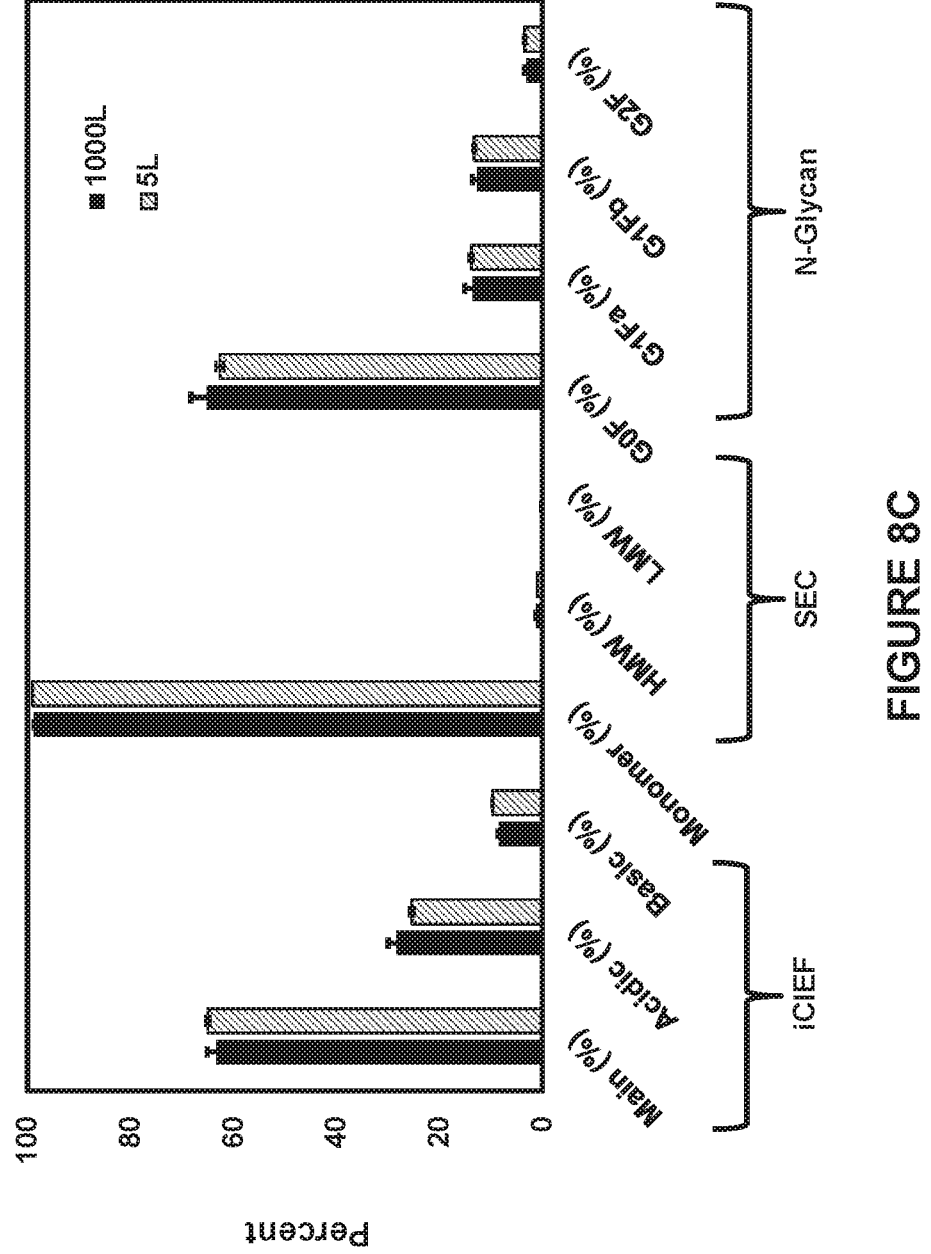
Figures 9A, 9B:
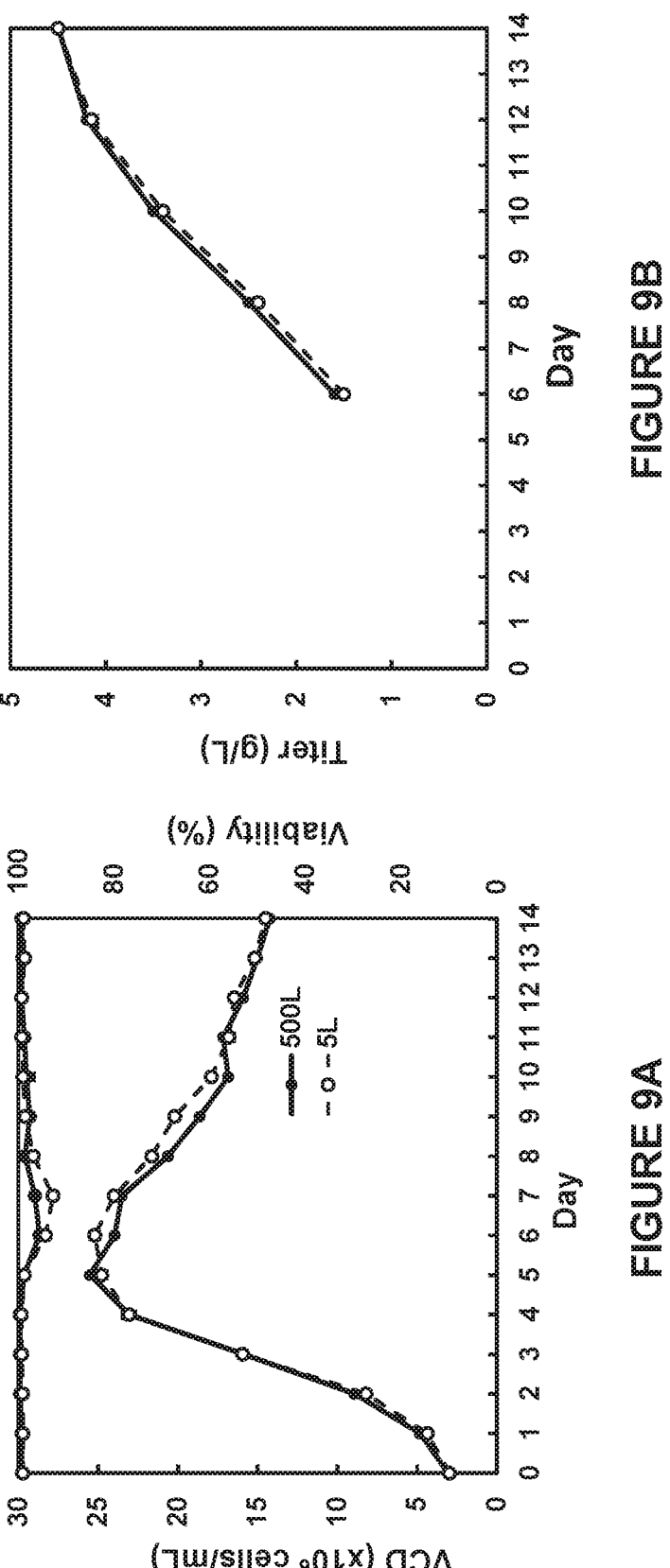
FIGS. 9A-9C.
Figure 9C:
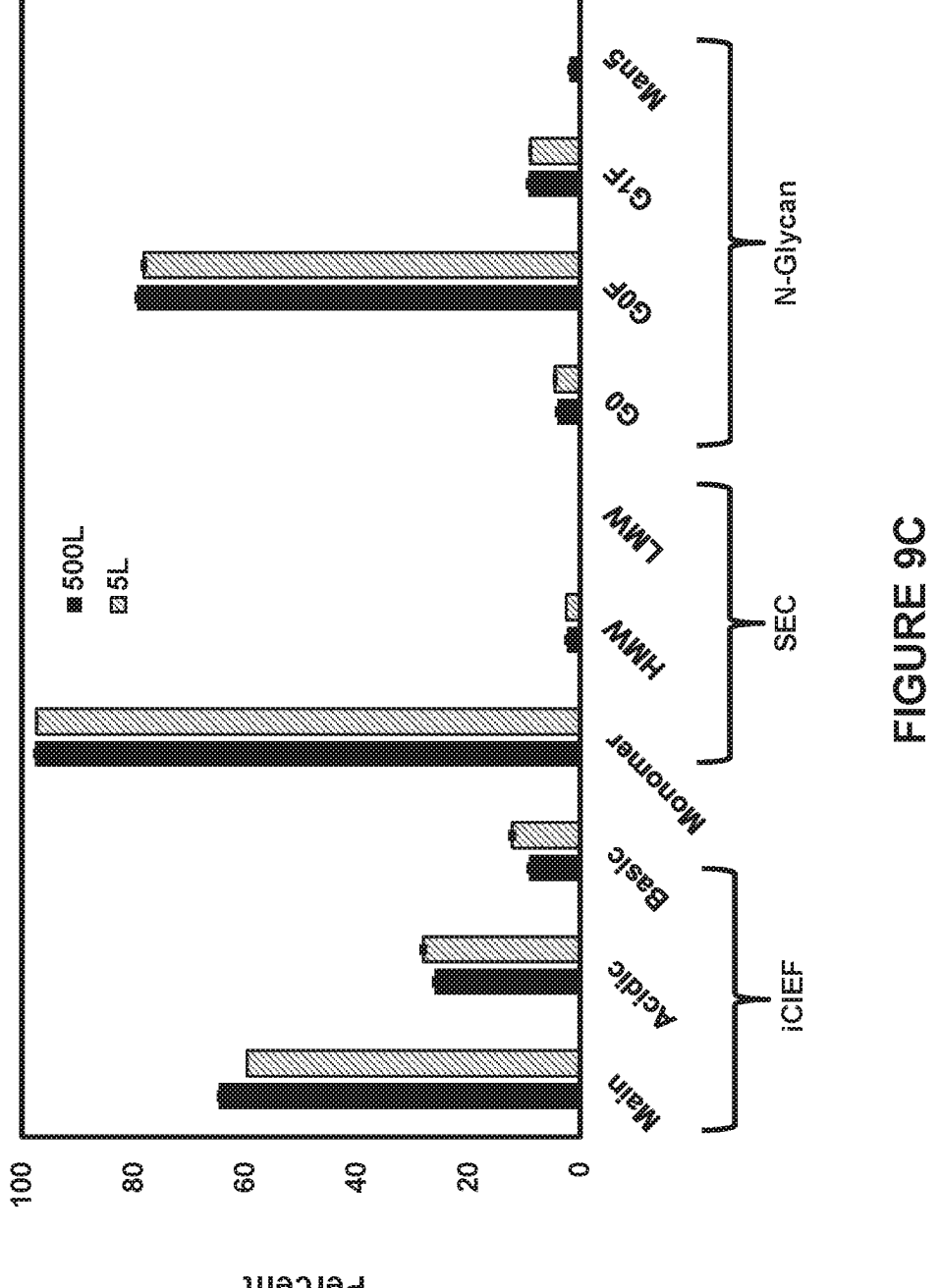
Figures 10A, 10B:
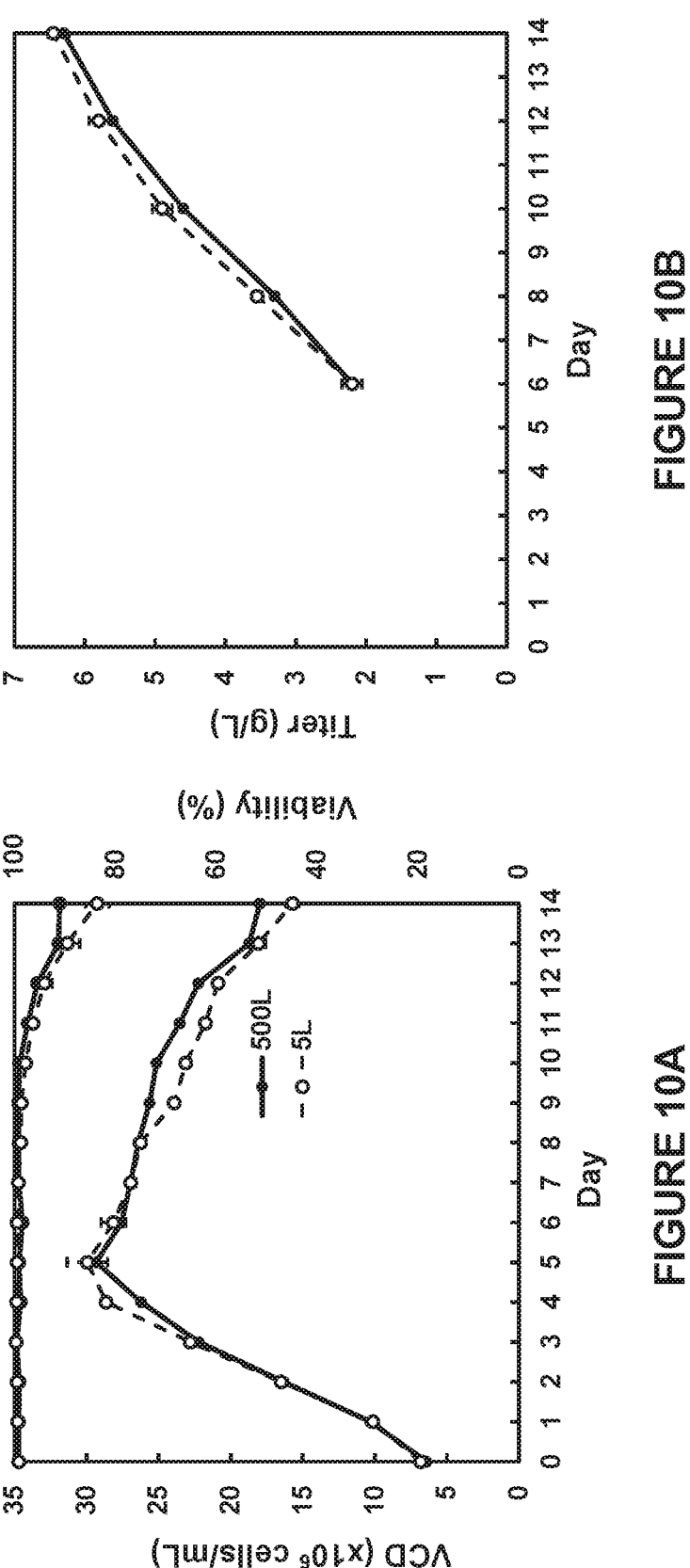
FIGS. 10A-10C.
Figure 10C:
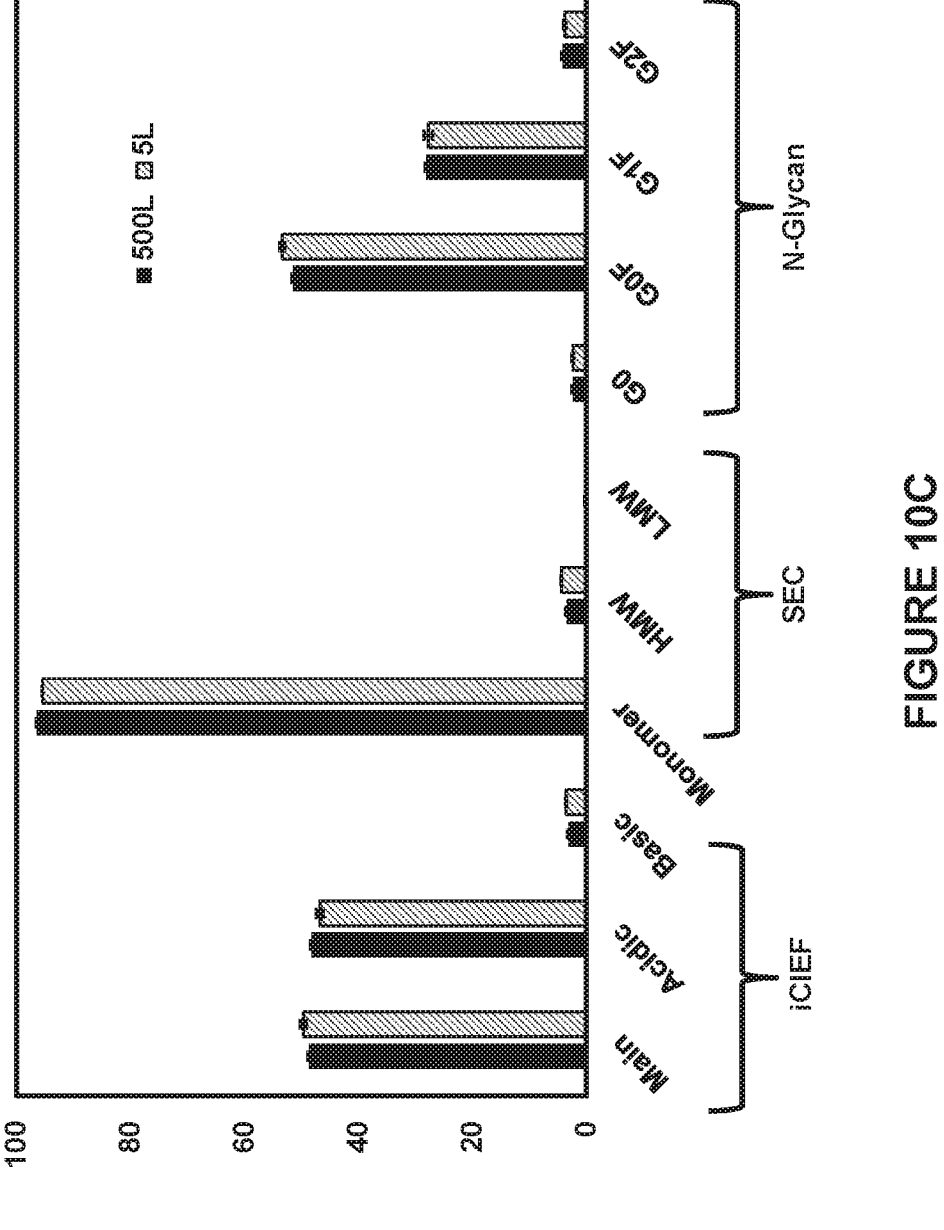

Large scale manufacturing processes for the three molecules were performed at Bristol-Myers Squibb's GMP facility either at 1000 L scale (for cell line A) or scale up facility at 500 L scale (for cell lines B and C). The N–1 seed cultures for cell lines A and B utilized the batch culture enriched with glucose and nutrients, whereas the N–1 seed for cell line C was cultivated in fed-batch mode. All three processes were shown to be robust and scalable to 1000 L or 500 L. The cell density, titer and product quality profiles are consistent with those of the satellite cultures in lab-scale bioreactors (FIGS. 8-10). For cell line A, the production cultures were harvested on day 10 due to the exceptionally high titer exceeding the capacity for downstream purification. The shortened culture duration for cell line A enabled a new production culture to be inoculated every week (with two production vessels), significantly increasing production output.

The invention claimed is:

1. A method for large-scale production of a recombinant polypeptide of interest comprising: (1) culturing a host cell expressing the recombinant polypeptide of interest in an N–1 stage, non-perfusion-based culture system, wherein the host cells are cultured in an enriched medium to obtain an N–1 stage viable cell density of at least $15\times10^6$ cells/mL, wherein the host cells are CHO cells; and (2) inoculating an N production culture system at high-seed density of at least $2\times10^6$ cells/mL with host cells from the N–1 stage, non-perfusion-based culture system, wherein the enriched medium comprises an increased amount of a carbon source relative to non-enriched medium, wherein the carbon source is glucose.

2. The method of claim 1, wherein the N production culture system is a fed-batch bioreactor.

3. The method of claim 2, wherein the fed-batch bioreactor is at least 1,000 L, at least 5,000 L, at least 10,000 L, at least 15,000 L, or at least 20,000 L.

4. The method of claim 1, wherein the enriched medium is enriched by a feed media at least 5%, at least 10%, at least 15%, at least 20% relative to non-enriched medium.

5. The method of claim 1, wherein the enriched medium further comprises an increased amount of nutrients relative to non-enriched medium, wherein the nutrients are selected from amino acids, lipids, vitamins, minerals, and polyamines.

6. The method of claim 1, wherein the titer of the polypeptide of interest is at least 100 mg/L, at least 1 g/L, at least 3 g/L, at least 5 g/L or at least 10 g/L.

7. The method of claim 1, wherein the host cell is cultured in a basal media or an enriched basal media to obtain an N production stage viable cell density of at least $5\times10^6$, or at least $10\times10^6$ viable cells per mL.

8. The method of claim 1, further comprising the step of isolating the polypeptide of interest, wherein the polypeptide of interest is an antibody or antigen-binding fragment.

9. The method of claim 8, wherein the antibody binds an antigen, wherein the antigen is PD-1, PD-L1, LAG-3, TIGIT, GITR, CXCR4, CD73 HER2, VEGF, CD20, CD40, CD11a, tissue factor (TF), PSCA, IL-8, EGFR, HER3, or HER4.

10. The method of claim 1, wherein the N production culture system is inoculated at high-seed density of at least $3\times10^6$ cells/mL with host cells from the N–1 stage, non-perfusion-based culture system.

11. The method of claim 1, wherein the N production culture system is inoculated at high-seed density of at least $5\times10^6$ cells/mL with host cells from the N–1 stage, non-perfusion-based culture system.

12. The method of claim 1, wherein the non-perfusion-based culture system is a batch bioreactor.

13. The method of claim 1, wherein the non-perfusion-based culture system is a fed-batch bioreactor.

* * * * *